United States Patent
Corydon et al.

(10) Patent No.: US 11,963,902 B2
(45) Date of Patent: Apr. 23, 2024

(54) STOMA COVER FOR COVERING A STOMA DURING AN EXCHANGE OF AN OSTOMY APPLIANCE

(71) Applicant: Coloplast A/S, Humlebaek (DK)

(72) Inventors: Marlene Corydon, Espergaerde (DK); Lars Olav Schertiger, Fredensborg (DK); Troels Jensen, Helsinge (DK); Joergen Daucke von Barner, Struer (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 18/205,594

(22) Filed: Jun. 5, 2023

(65) Prior Publication Data

US 2023/0320891 A1    Oct. 12, 2023

Related U.S. Application Data

(63) Continuation of application No. 16/962,512, filed as application No. PCT/DK2019/050012 on Jan. 14, 2019, now Pat. No. 11,707,378.

(30) Foreign Application Priority Data

Jan. 19, 2018   (DK) ............................ PA 2018 70034

(51) Int. Cl.
*A61F 5/445*    (2006.01)
*A61F 5/44*    (2006.01)

(52) U.S. Cl.
CPC ............ *A61F 5/445* (2013.01); *A61F 5/4401* (2013.01); *A61F 5/4407* (2013.01); *A61F 2005/4402* (2013.01); *A61F 2005/4455* (2013.01)

(58) Field of Classification Search
CPC ...... A61F 5/445; A61F 5/4401; A61F 5/4407; A61F 2005/4402; A61F 2005/4455
See application file for complete search history.

(56) References Cited

U.S. PATENT DOCUMENTS

| | | | | |
|---|---|---|---|---|
| 2,448,938 | A | * | 9/1948 | Anthony ................. A61F 13/10 604/355 |
| 3,123,074 | A | * | 3/1964 | Turner .................... A61F 5/442 604/332 |
| 3,520,301 | A | | 7/1970 | Fenton |

(Continued)

FOREIGN PATENT DOCUMENTS

| | | |
|---|---|---|
| CN | 201676055 U | 12/2010 |
| CN | 104382683 A | 3/2015 |

(Continued)

*Primary Examiner* — Guy K Townsend
(74) *Attorney, Agent, or Firm* — Coloplast Corp., Coloplast A/S; Nick Baumann

(57) ABSTRACT

A stoma cover includes a hood and an adjustment band. The hood extends between a proximal end and a closed distal end. The adjustment band is connected to the proximal end. The adjustment band allows the hood to adjust between a first open size at the proximal end that is sized for placement over the stoma and a second size that is smaller than the first open size. The second size is adapted to secure the hood relative to a root portion of the stoma. A moisture absorbing material is disposed inside of the hood, where the moisture absorbing material is provided to absorb stomal output exuding from a meatus of the stoma.

13 Claims, 17 Drawing Sheets

(56) References Cited

U.S. PATENT DOCUMENTS

| | | | |
|---|---|---|---|
| 3,548,828 A * | 12/1970 | Vasile | A61F 5/451 604/328 |
| 3,938,521 A * | 2/1976 | Ritota | A61F 5/455 604/328 |
| 4,117,847 A * | 10/1978 | Clayton | A61F 5/4408 604/179 |
| 4,187,850 A * | 2/1980 | Gust | A61F 5/445 604/338 |
| 4,205,678 A * | 6/1980 | Adair | A61F 5/448 604/343 |
| 4,344,433 A * | 8/1982 | Smith | A61F 5/445 604/344 |
| 4,344,435 A * | 8/1982 | Aubin | A61M 39/0247 604/246 |
| 4,368,733 A * | 1/1983 | Sanidas | A61G 9/00 604/327 |
| 4,686,355 A | 8/1987 | Lay | |
| 4,701,168 A * | 10/1987 | Gammons | A61M 35/006 604/1 |
| 4,726,354 A * | 2/1988 | Fujita | A61F 5/445 600/32 |
| 4,850,986 A * | 7/1989 | Temple | A61F 5/44 604/355 |
| 5,125,916 A * | 6/1992 | Panebianco | A61F 5/445 604/328 |
| 5,312,384 A * | 5/1994 | Temple | A61F 5/44 604/355 |
| 5,474,179 A * | 12/1995 | Iosif | A61F 5/451 206/521 |
| 6,328,720 B1 * | 12/2001 | McNally | A61J 15/0015 604/335 |
| 6,409,709 B1 * | 6/2002 | Recto | A61F 5/445 604/338 |
| 6,569,081 B1 | 5/2003 | Nielsen et al. | |
| 6,916,312 B2 | 7/2005 | Kondo et al. | |
| 6,929,627 B2 * | 8/2005 | Mahoney | A61F 5/445 606/108 |
| 8,343,119 B2 * | 1/2013 | Mayer | A61F 5/443 604/338 |
| 9,078,990 B1 * | 7/2015 | Obst | A61M 27/00 |
| 10,130,505 B2 * | 11/2018 | Guidry | A61F 5/443 |
| 10,357,394 B2 * | 7/2019 | Guidry | A61F 5/445 |
| 10,478,328 B2 * | 11/2019 | Guidry | A61F 5/445 |
| 10,792,472 B2 * | 10/2020 | Shankarsetty | A61B 17/1114 |
| 10,813,787 B2 * | 10/2020 | Dinakara | A61F 5/445 |
| 11,148,845 B1 * | 10/2021 | Ellis | A61F 5/445 |
| D939,696 S * | 12/2021 | Uridil | A61F 5/445 |
| 11,207,205 B2 * | 12/2021 | Tan | A61F 5/445 |
| 11,291,576 B2 * | 4/2022 | Miller | A61F 5/4401 |
| 11,504,263 B2 * | 11/2022 | Hrushka | A61F 5/443 |
| 2003/0040727 A1 | 2/2003 | Boulanger et al. | |
| 2003/0204175 A1 * | 10/2003 | Mahoney | A61F 5/445 604/345 |
| 2004/0260257 A1 * | 12/2004 | Ciok | A61F 5/448 604/332 |
| 2007/0149935 A1 * | 6/2007 | Dirico | A61F 5/453 604/347 |
| 2008/0103463 A1 | 5/2008 | Tsai et al. | |
| 2008/0269698 A1 * | 10/2008 | Alexander | A61F 5/445 604/332 |
| 2010/0022975 A1 * | 1/2010 | Vanden Bosch | A61F 5/445 604/338 |
| 2010/0145292 A1 * | 6/2010 | Mayer | A61F 5/445 604/337 |
| 2010/0170518 A1 | 7/2010 | Goldberg | |
| 2012/0277700 A1 * | 11/2012 | Amer, Jr. | A61F 5/445 604/332 |
| 2015/0265455 A1 | 9/2015 | Fernandez et al. | |
| 2017/0156917 A1 * | 6/2017 | Guidry | A61F 5/4404 |
| 2017/0367871 A1 * | 12/2017 | Dinakara | A61F 5/445 |
| 2018/0028347 A1 * | 2/2018 | Guidry | A61F 5/4407 |
| 2018/0236207 A1 * | 8/2018 | Shankarsetty | A61B 17/1114 |
| 2018/0289527 A1 * | 10/2018 | Vila | A61F 5/445 |
| 2018/0369011 A1 * | 12/2018 | Pickens | A61F 5/4408 |
| 2019/0015241 A1 * | 1/2019 | Lin | A61F 5/4404 |
| 2019/0038452 A1 * | 2/2019 | Aravalli | A61F 5/445 |
| 2019/0262167 A1 * | 8/2019 | Guidry | A61F 5/445 |
| 2020/0038227 A1 * | 2/2020 | Makar, Jr. | A61F 5/445 |
| 2020/0046542 A1 * | 2/2020 | Guidry | H05B 1/025 |
| 2020/0085608 A1 * | 3/2020 | Hrushka | A61F 5/4401 |
| 2020/0281758 A1 * | 9/2020 | Tan | B33Y 80/00 |
| 2021/0000632 A1 * | 1/2021 | Nielsen | A61F 5/443 |
| 2021/0085513 A1 * | 3/2021 | Corydon | A61F 5/4401 |
| 2021/0244497 A1 * | 8/2021 | Taweh | A61F 5/445 |
| 2021/0251796 A1 * | 8/2021 | Holroyd | A61F 5/445 |
| 2021/0251797 A1 * | 8/2021 | Holroyd | A61F 5/4405 |
| 2021/0369492 A1 * | 12/2021 | O'Grady | A61M 39/0247 |
| 2022/0168131 A1 * | 6/2022 | Heckler | A61F 5/449 |
| 2022/0280331 A1 * | 9/2022 | Stroebech | A61F 5/449 |

FOREIGN PATENT DOCUMENTS

| | | | | |
|---|---|---|---|---|
| CN | 204181773 U | 3/2015 | | |
| CN | 204274747 U | 4/2015 | | |
| FR | 2816202 A1 | 5/2002 | | |
| GB | 2425482 A | 11/2006 | | |
| GB | 2491161 A | 11/2012 | | |
| JP | S6232023 A | 2/1987 | | |
| JP | 3123094 U | 7/2006 | | |
| WO | 1983001378 A1 | 4/1983 | | |
| WO | WO-2010065715 A2 * | 6/2010 | | A61F 5/443 |

* cited by examiner

STOMA COVER FOR COVERING A STOMA DURING AN EXCHANGE OF AN OSTOMY APPLIANCE

BACKGROUND

When users of an ostomy appliance are in the process of changing their appliance, they often experience difficulties in cleaning the area around the stoma, such as the peristomal area, because of leakage of output from the stoma during the cleaning and exchange process. A stoma does not have a sphincter enabling the user's body to the close off the stoma during the time it takes to exchange the appliance. Particularly, uro-(urinary) and ileostomies (small intestine) leak more or less fluid output almost continuously, making it difficult for the user to obtain a clean and dry skin area, which is needed for providing a good base for attachment of a new ostomy appliance to the skin surface. Stomal output often contains fluids and visceral contents that are very aggressive to both the skin of a user and to ostomy devices.

Users and health care professionals alike would welcome improvements in solutions to better alleviate such problems.

SUMMARY

The present disclosure provides aspects and embodiments of a system for applying a stoma cover according to claim 1. A stoma cover and a kit of parts, including the system for applying a stoma cover, are also disclosed.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
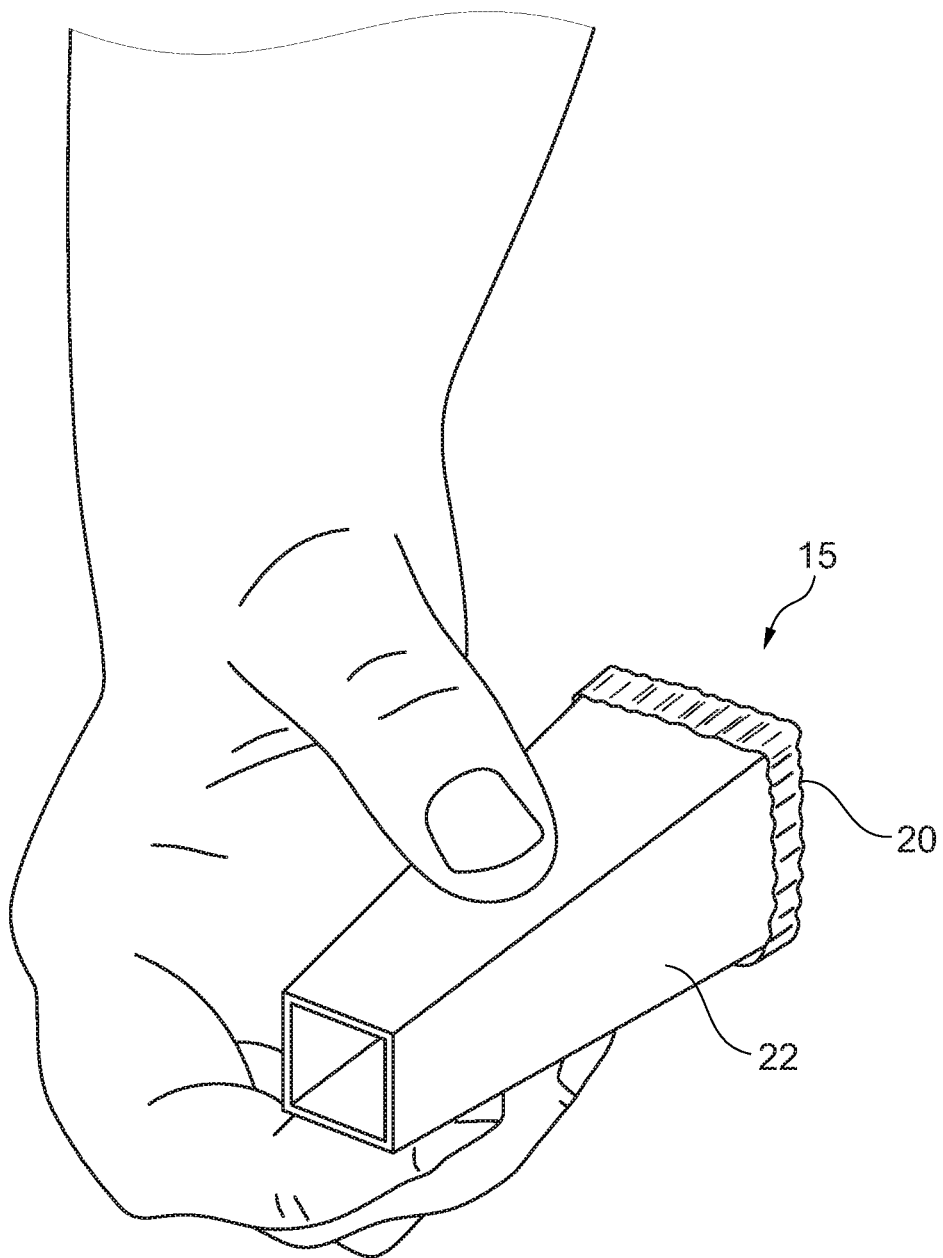
FIG. 1 is a schematic, perspective view of one embodiment of a system for applying a stoma cover.

In the following Detailed Description, reference is made to the accompanying drawings, which form a part hereof, and in which is shown by way of illustration specific embodiments in which the invention may be practiced. In this regard, directional terminology, such as "top", "bottom", "front", "back", "leading", "trailing", etc., is used with reference to the orientation of the Figure(s) being described. Because components of embodiments can be positioned in several different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary aspects and embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating or exuding from the stoma may be referred to as both stomal "output", "waste(s)" and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a device or part of a device, the referral is to the skin-facing side, when the ostomy appliance is worn by a user. Likewise, whenever referring to the distal side or surface of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

In this disclosure, the longitudinal direction is to be considered the direction in relation to an element or component (or other) which extends between the ends or end portions of a longest dimension of the element or component. In some instances, the longitudinal direction can be understood to correspond to the axial direction mentioned above.

The radial direction is defined as transverse to the axial direction, i.e. transverse to the direction of the stoma. Similarly, the term "radial direction" can also be used in relation to being transverse to the longitudinal direction of an element or component. In some sentences, the words "inner" and "outer" may be used. These qualifiers should generally be perceived with reference to the radial direction, such that a reference to an "outer" element means that the element is farther away from a centre portion of a thing, such thing e.g. being an element or component of an ostomy appliance than an element referenced as "inner". In addition, "innermost" should be interpreted as the portion of a component forming a centre of the component and/or being adjacent to the centre of the component. In analogy, "outermost" should be interpreted as a portion of a component forming and/or including an outer edge or outer contour of a component, and/or being adjacent to that outer edge or outer contour.

In this disclosure, the feature "hood-like element" is intended to mean a flexible covering for a thing, herein the "thing" is the stoma, and the "hood-like element" could for visualization purposes be compared to a cover or sack used on the head of a falcon to keep it quiet, when the bird is not pursuing game (compare: keeping the stoma "quiet").

The use of the phrase "substantially" as a qualifier to certain features or effects in this disclosure is intended to mean that any deviations are within tolerances, such as manufacturing tolerances, that would normally/be expected by the skilled person in the relevant field.

The use of the word "generally" as a qualifier to certain features or effects in this disclosure is intended to mean—for a structural feature: that a majority or major portion of such feature exhibits the characteristic in question, and—for a functional feature or an effect: that a majority of outcomes involving the characteristic provide the effect, but that exceptionally outcomes do not provide the effect.

The use of the word "essentially" as a qualifier to certain structural and functional features or effects in this disclosure is used for emphasizing what is the most important focus of something or fact about something—for example, a feature may have or fulfil a variety of effects, but when the disclosure discusses one effect as being "essentially" provided, this is the focus and the most important effect in relation to the present disclosure.

In one aspect, the present disclosure relates to a system for applying a stoma cover over a stoma of a user including an applicator and a releasable stoma cover. The releasable stoma cover includes a hood-like element including a proximal end portion and a distal end portion. The releasable stoma cover is defining a generally longitudinal direction between the first and the second end portions. The proximal end portion of the hood-like element is configured to be adjustable at least in a direction transverse to the longitudinal direction. This provides inter alia for a stoma entrance of the stoma cover to be of variable size. The distal end portion of the hood-like element is configured as a closed end portion. There is no stoma entrance or similar opening in the closed distal end portion of the hood-like element. The term "releasable" should be understood in relation to the stoma cover being able to be released from the applicator.

The applicator of the system is configured to receive and hold the proximal end portion of the hood-like element in an expanded disposition. This allows the hood-like element to be located over the stoma of the user, which provides for the stoma of the user to be receivable through the stoma entrance. In some cases, an entirety of a stoma protruding from the skin surface is received through the stoma entrance and inside the hood-like element. In other instances, at least a distal portion of the protruding stoma including the meatus or "mouth" of the stoma is received through the stoma entrance and inside the hood-like element. It is to be observed that the hood-like element of the stoma cover receives the stoma, in such a way that any stomal output leaving the stoma (from the meatus or "mouth") is directed to the inside of the hood-like element.

Moreover, the applicator of the system is manipulable to release the proximal end portion of the hood-like element from the hold in the expanded disposition. By manipulation of the applicator, the proximal end portion of the hood-like element can be released from the hold in the expanded disposition, which allows the stoma cover to be released from the applicator to cover the stoma of the user.

The system for applying a stoma cover of the present disclosure provides an easily applicable and intuitive way of applying a stoma cover in a fast and reliable manner. Moreover, the stoma cover of the system is a temporary stoma cover adapted to provide the user with a temporary closure of the stoma, so that the user can clean and dry the skin area surrounding the stoma prior to attaching a new ostomy appliance without any risk of the skin area being soiled by stomal output before the new appliance is attached. A clean and dry skin area in turn has the positive effect that an adhesive flange on a new ostomy appliance to be applied connects better to the skin surface, which makes the new ostomy appliance less prone to subsequent leakage issues (due to failing adherence of the flange to the skin). In some implementations of the present disclosure, the stoma cover is left in place over the stoma even during application of the new ostomy appliance to the skin surface around the stoma. Providing a stoma cover which is adapted to be left in place over the stoma is advantageous in that it similarly helps make the new ostomy appliance less prone to subsequent leakage issues caused by accidental soiling of the adhesive plate during application.

The system is further advantageous and useful in that it allows a user to apply a stoma cover without having to directly hold the stoma cover to be applied (such as between the fingers of one hand), and without having to touch either the stoma itself or the surrounding skin surface. This greatly reduces any likelihood of soiling the user's fingers and/or any accessories or components of the new ostomy appliance to be applied during the ostomy appliance exchange. This in turn also reduces the risk of bacterial contamination of the skin, the clothes of the user, accessories, other components of an ostomy appliance, sink, wash basin, faucets etc., stemming from such soiling of the fingers. The system generally facilitates easy handling of a temporary stoma cover. Similar advantages are evident if a HCP applies the stoma cover to the stoma instead of the user him- or herself.

In the expanded disposition of the adjustable proximal end the stoma entrance to the stoma cover is adapted to be adequately opened to a first size for receiving a target stoma, such that the stoma cover can be applied over the stoma and moved towards the skin surface of the user with the stoma (or at least a distal portion thereof) entering an inside of the hood-like element through the stoma entrance. The greatest (largest) achievable first size of the stoma entrance can be decided and controlled at manufacture of the stoma cover and the applicator of the system. Such a maximum size will be dependent inter alia on the size and/or nature of a target stoma. Therefore, a stoma cover and an applicator of the disclosed system can be manufactured in a variety of sizes corresponding to ranges of different stoma sizes and/or the nature of the stomas.

In the non-expanded disposition, the stoma entrance at the adjustable proximal end portion can be adapted to have a second size, which is smaller than the first size. This smaller size corresponds to a smaller circumferential length of the stoma entrance, reflecting the situation wherein the stoma cover is not received in the applicator. Thereby, the adjustable proximal end portion of the stoma cover can be closer to, or move nearer to, the stoma itself, such as nearer to a root portion of the stoma (the root portion understood as being approximately at level with the skin surface of the user). Thereby, the stoma is received in an inside of the hood-like element of the stoma cover, which helps to prevent stomal output from escaping out of the stoma cover during exchange of the ostomy appliance. In embodiments, a portion of the adjustable proximal end portion includes at least a peripheral edge surrounding the stoma entrance, which peripheral edge is adapted to engage with a mucous membrane surface of the stoma itself to further secure against stomal output escaping or seeping out of the stoma cover. However, in such implementations, it should be observed that any potential force acting on the mucous membrane surface of the stoma by engagement with the peripheral edge, is not so large as to cause strangulation of the stoma (a condition where blood supply to the stomal tissue is hindered).

In embodiments, the applicator is configured to receive and hold the adjustable proximal end portion of the hood-like element in the expanded disposition by including a resilient component. In embodiments, the applicator is adapted to maintain, or keep, the adjustable proximal end portion of the hood-like element in a state of tension, the state of tension achievable because of the nature of the resilient component of the adjustable proximal end portion of the hood-like element. This means that the first size of the stoma entrance formed at the adjustable proximal end portion of the hood-like element is bigger, than the second (relatively smaller) size of the stoma entrance present, when the adjustable proximal end portion is in the non-expanded disposition. In such embodiments, the non-expanded disposition can alternatively, or additionally, be understood as corresponding to a relaxed or unstrained state of the resilient component of the adjustable proximal end portion of the stoma cover.

In embodiments, the resilient component provides for the adjustable proximal end portion of the hood-like element to be resilient at least in a direction transverse to the longitudinal direction. In embodiments, the resilient component includes an anisotropic material, adapted to provide resiliency in the transverse direction (transverse to the longitudinal direction of the hood-like element), while not providing any resiliency in the direction perpendicular to the transverse direction, i.e. in the longitudinal direction. Suitable anisotropic materials can include a polymer film, coating, woven, non-woven, fibre, knit, fabric, textile, laminate or foam or combinations thereof. In embodiments, the anisotropic material is a polyurethane film optionally a laminate or a co-extruded film. In embodiments, the anisotropic material includes a multi-layer film.

In embodiments, the adjustable proximal end portion of the hood-like element is configured to be adjustable in all directions. In one implementation of such embodiments, the adjustable proximal end portion of the hood-like element includes an elastic material, such as an elastic material layer, providing resiliency in all directions.

The distal end portion of the hood-like element is configured to form a closed end portion of the hood-like element. In embodiments, the hood-like element has a generally conical shape. In embodiments, the hood-like element forms a sidewall, such as an annular sidewall, tapering from a first largest width of the hood-like element at a proximal-most end thereof, to a smallest width at a distal-most end of the hood-like element. In embodiments, the smallest width at the distal-most end is configured to practically "zero", corresponding to the distal-most end being an apex of the hood-like element. In embodiments, the tapering sidewall of the hood-like element is provided as being gradually tapering, such as (but not limited to) including two or more portions provided stepwise. In embodiments, a distal-most portion of the sidewall includes the distal-most end of the hood-like element and forms the closed end portion.

In embodiments, the resilient component of the adjustable proximal end portion of the hood-like element is stretchable, which provides for a first size of the stoma entrance in a stretched-out disposition to be stretched and be bigger than a second size of the stoma entrance in a non-stretched disposition. In embodiments, the resilient component is integrated in the adjustable proximal end portion of the hood-like element. In embodiments, the resilient component is integrated in, or with, a sidewall of the hood-like element at the adjustable proximal end portion thereof. In embodiments, the hood-like element includes two or more resilient components. This can include providing a resilient component at other and/or additional portions of the hood-like element than at the adjustable proximal end portion.

In embodiments, the resilient component comprises an elastic thread. In embodiments, the elastic thread includes one or more filaments in a side-by-side relationship, the filaments being optionally further intertwined with each other. In embodiments, the resilient component includes an elastic band. Other suitable configurations of the resilient component in the form of an elastic thread or band, including providing one or more elastic threads or bands and/or combining them, are also acceptable.

In embodiments, the adjustable proximal end portion of the hood-like element includes a pulling strip, which is configured to reduce the size of the stoma entrance when the pulling strip is pulled. In embodiments, the pulling strip is configured to include a noose or snare or loop-like portion, such that a pull exerted on a free end of the pulling strip causes a tightening of the noose- or snare-like portion.

In embodiments, the adjustable proximal end portion of the hood-like element is configured to include at least one pocket in which pocket at least one elastic strip or band (or other elastic and stretchable entity) is provided to form a resilient component of the hood-like element. In embodiments including a pulling strip, the pulling strip can be provided in the pocket. In embodiments, the elastic strip or band, respectively the pulling strip, is loosely provided inside the pocket. In embodiments, the at least one pocket is configured at or near (adjacent to) the peripheral edge of the adjustable proximal end portion forming the stoma entrance of the stoma cover.

In embodiments, the at least one pocket is an annular pocket (such as in embodiments wherein the hood-like element includes an annular sidewall). In embodiments, the annular pocket is formed by folding over the adjustable proximal end portion of the hood-like element and attaching the folded-over end portion to a sidewall of the hood-like element.

In embodiments including a resilient component, the elastic strip or band can be adapted to form a closed loop string or thread provided in the annular pocket.

In embodiments including a pulling strip, at least a pull or free end portion of the pulling strip is adapted to stick out of (extend from) the annular pocket. In embodiments, the annular pocket can include one or more zones in which the annular pocket is open, so that one or more portions of the loop string or thread, respectively the pulling strip, is exposed and/or can be engaged from the outside, such as by the fingers of a user or by a tool. In embodiments, the exposed one or more portions includes a pull end portion of the elastic strip, band or pulling strip sticking or extending out of the pocket, which pull end portion allows for tightening of the elastic thread, band or pulling strip at the root of the stoma. The pull end portion can include a safety stop means to avoid the possibility of strangulation of the stoma.

In embodiments, the pulling strip is configured to prevent the size of the stoma entrance from re-expanding. This is to be understood such that, after adjustment of the size of the stoma entrance by pull on the pulling strip to a certain second size, the size of the stoma entrance cannot be adjusted back to a larger size (such as the first, largest size of the stoma entrance). In embodiments, the pulling strip includes a buckle (or tensioning) portion and a strap portion extending from a first side of the buckle portion. In embodiments, a longitudinal extent of the strap portion is between 2-10 times a largest dimension of the buckle portion. In embodiments, the strap portion includes a plurality of barbs or saw tooth-like projections configured to combine with a through-going slit or opening provided in the buckle portion. In embodiments, each of the plurality of barbs or saw tooth-like projections extends from an edge of the strap portion. In other embodiments, each of the plurality of barbs or saw tooth-like projections extends from a planar surface of the strap portion. In embodiments, the buckle portion includes two or more slits or openings to allow for some flexibility. The slit or opening is dimensioned to allow the strap portion to enter through it, but also to prevent the strap portion from exiting out of the slit again. The strap portion is adapted to provide for the pulling strip to extend around the root of the stoma and enter through the slit in the buckle portion. The combination of the barbs or saw tooth-like projections on the strap portion with the through-going slits or openings allows for adjustment of the size of the stoma entrance and further prevents the size of the stoma entrance from re-expanding. In embodiments, a segment of the strap portion closest to the first side of the buckle portion is dimensioned to be unable to enter through the slit or opening in the buckle portion, thereby providing one embodiment of a safety stop means for preventing strangulation of the stoma from an excessive pull on the pulling strip.

In embodiments, the pulling strip is integrated in the adjustable proximal end portion of the hood-like element. In embodiments, the pulling strip is integrated in, or with, a sidewall of the hood-like element at the adjustable proximal end portion thereof.

In embodiments, the hood-like element is adapted to be flushable. Thereby, the stoma cover of the system, adapted to temporarily cover a stoma during exchange of ostomy appliance, can be left in place over the stoma, even when the new ostomy appliance is being applied to the skin surface. In embodiments, the hood-like element is adapted to either automatically release from the stoma after a period, and simply drop into a collecting bag of the ostomy appliance, or to be manipulated by the user to release from the stoma and drop into the bag. In embodiments, the period in which the stoma cover stays attached to the stoma can be configured to depend on a capacity of a moisture absorption material included in the hood-like element.

In this disclosure, it is to be noted that the feature "flushable" is not to be interpreted as "being dissolvable in water within minutes or even seconds." The flushable hood-like element is therefore not adapted to be dissolvable inside the collecting bag of the ostomy appliance. On the other hand, the flushable hood-like element is configured to be (-come) adequately pliable to be flushed out via a toilet and into the sewer system, when in prolonged (relatively long in duration) contact with moisture and/or stomal output, such as when the hood-like element is dropped in the collecting bag. The flushable hood-like element can further be configured to be biodegradable over an extended time frame once in the sewer system (i.e. once the hood-like element has been used and discarded by the user). In embodiments, the flushable hood-like element includes one or more water soluble and/or biodegradable polymers, e.g. polyvinyl alcohol materials (PVOH), cellulose and its derivatives, which can suitably be used to configure the flushable hood-like element to be softened when brought into contact with moisture or liquid, but also to not dissolve (and/or lose structural integrity) within a short period of time, such as a period of time required to use the stoma cover temporarily during exchange of an ostomy appliance (see elsewhere in the disclosure for concrete time requirements).

It is a particularly advantageous effect of the flushable hood-like element of the stoma cover of the system that it can be left in place over the stoma even during application of the new ostomy appliance. This provides the advantage that any moisture including mucus exuding from the mucus membrane of the stoma cannot come into contact with the adhesive surface of the new ostomy appliance, when the new appliance is being applied to the skin surface around the stoma. While applying a new appliance, the stoma must enter through a stoma-receiving opening in an adhesive plate of the new appliance. Applying the adhesive plate around the stoma without accidentally coming into contact with the mucus membrane of the stoma can be extremely challenging and difficult to users, particularly users suffering from reduced dexterity, or having other or additional handicaps. Providing a stoma cover which is adapted to be left in place over the stoma (thus covering the mucus membrane) according to the disclosure is thus clearly advantageous and further helps make the new ostomy appliance less prone to subsequent leakage issues caused by accidental soiling of the adhesive plate during application.

It is further envisioned that the option of leaving the flushable hood-like element of the stoma cover in place over the stoma during application of a new ostomy appliance, additionally or alternatively provides the advantage of enabling the user to apply the new appliance more controllably. This is believed to at least partly be caused by the user experiencing an improved tactile feel of the location of the stoma and/or an improved visualization in the user's mind of the three-dimensional peristomal skin area. Being in more control provides for the user to more accurately position the new appliance, incl. by not touching the stoma and by centring the adhesive plate of the appliance better around the stoma. This more accurate application of the new ostomy appliance in turn provides for reducing the probability of leakage. The more accurate application is even further amplified by the avoidance of getting mucus from the mucus membrane of the stoma onto the adhesive plate during the application of the new appliance, and as such therefore provide particularly advantageous synergistic effects.

In embodiments, the flushable hood-like element includes a pulling strip provided in engagement with and around an external surface of the proximal end portion of the hood-like element. In embodiments, the pulling strip is configured to be flushable. In embodiments, the flushable pulling strip suitably comprises the same material(s) as the flushable hood-like element.

In embodiments, the hood-like element includes two or more materials. The two or more materials can advantageously provide the hood-like element with two or more different desired characteristics. Examples of such different characteristics include, but are not limited to: resiliency/elasticity, strength, moisture permeability, moisture absorption, liquid barrier, moisture barrier and odour barrier, design, sensitivity including feel of abrasion or friction resistance and others. In embodiments, the two or more materials are provided in layers.

In embodiments, the two or more material layers are provided in an overlapping, or at least partly overlapping, "layered" relationship with each other. In embodiments, the two or more material layers are provided in a side-by-side relationship with each other. Combinations of the ways of providing the layers with respect to each other, are also acceptable.

In embodiments including a resilient component, suitable materials for the two or more material layers include natural or synthetic elastomers such as, but not limited to, natural rubber and thermoplastic elastomers (TPE). In embodiments in which the hood-like element is flushable, suitable materials for the two or more material layers include, but are not limited to, natural or synthetic elastomers such as, but not limited to, natural rubber and thermoplastic elastomers (TPE). In embodiments, the resilient component materials can comprise one or more threads or bands or similar instead of being provided in layers.

In embodiments, the hood-like element comprises a moisture absorbing material. Suitable materials for the moisture absorption material can be selected from the group including cellulose, polyethylene terephthalate (PET), polypropylene (PP), polyvinyl alcohol (PVOH) or combinations thereof, e.g. provided in the form of a non-woven material component. Other suitable materials include cotton wool, fleece of cellulose fibres and foams, such as open-celled foams including foams of polyethylene (PE), polyurethane (PU) and ethylene vinyl acetate (EVA), and/or combinations thereof.

In embodiments, the hood-like element includes at least a non-woven material, an absorbing material and a moisture impermeable material. The moisture impermeable material is configured to retain any liquid components of the stomal output or mucus, such that these liquid components cannot escape the hood-like element.

Suitable materials for the moisture impermeable (liquid retaining) material include, but are not limited to, PE, PP and TPE and/or combinations thereof. In embodiments, the non-woven material, absorbing material and moisture impermeable material are provided in layers in a "layered" relationship with each other, substantially completely overlapping each other, and combining to form a sidewall of the hood-like element. In embodiments, the non-woven material layer functions as a carrier layer providing a reinforcing nature of the sidewall and helping to carry the absorbing material layer and the moisture impermeable material layer. In embodiments, the moisture impermeable material layer is provided as a middle or intermediate layer between the non-woven material layer and the moisture absorption layer. The moisture impermeable material ensures that any moisture and/or stomal output is prevented from escaping through the sidewall of the hood-like element, thereby preventing stomal output from reaching the surroundings. In embodiments, individual layers of the hood-like element are attached to each other using an adhesive material or by providing one or more welds or weld zones. Other ways of attaching individual layers of the hood-like element to each other are acceptable.

In embodiments of the hood-like element of the stoma cover, the non-woven layer is adapted to form an outermost layer of the hood-like element, towards the external surroundings of the hood-like element, and the moisture absorption layer is adapted to form an innermost layer of the hood-like element of the stoma cover. In such embodiments, the moisture impermeable layer forms an intermediate layer of the hood-like element. In embodiments, the moisture impermeable layer includes a semipermeable material allowing air of the surrounding atmosphere to enter an inside of the hood-like element, and simultaneously prevents moisture and solids, such as the components of stomal output, from exiting from the inside of the hood-like element to the surroundings with the risk of soiling.

The moisture absorption material (layer) of the hood-like element is configured to absorb stomal output exuding from the meatus of the stoma, when the stoma cover is applied to the stoma during exchange of an ostomy appliance. Particularly, but not exclusively, the moisture absorption (layer) absorbs the fluid components of the stomal output. In the cases of users having an ileostomy or a urostomy, the fluid components correspond to a major part or an entirety of the stomal output, whereas in the case of a user having a colostomy, a larger percentage of the stomal output will be in solid form. An additional advantage of the moisture absorption material (layer) is that it acts to also "pull" the hood-like element closer to the stoma, because of capillary action forces between the moisture absorption material and moisture/mucus on the mucus membrane of the stoma. This capillary action helps provide for the stoma cover to advantageously be pulled ("drawn" or "sucked") onto the stoma, thereby facilitating both the stoma cover's release from the applicator of the system and helping to keep the stoma cover in place over the stoma during exchange of the ostomy appliance.

An even further advantage of the capillary action of the moisture absorption material (layer) is to help adjust the hood-like element including the size of the stoma entrance to adapt it to the individual stoma, such that the hood-like element can be brought into a snug fit with the stoma as soon as the applicator is manipulated. The release of the stoma cover from the applicator over (onto) the stoma is thus particularly easy and controllable, due to the combined effects described, which aid in releasing the stoma cover from the applicator.

In addition to the capillary action, the user can advantageously help to snug fit the stoma cover over the stoma, when it has been released from the applicator, by exerting a relatively light finger-pressure on the outside of the stoma cover, thereby shortening the time of achieving an optimal fit of the stoma cover to the stoma.

Furthermore, experiments have shown that a stoma cover according to the disclosure, when applied over a stoma, is to a surprisingly high degree capable of withholding even larger portions (or bursts) of stomal output from escaping the intestine via the stoma. In other words, the experiments have revealed that the temporary stoma cover of the disclosure remains in place over the stoma, even when a significant pressure from the bowels may be exerted on it.

In embodiments, an absorption capacity of the moisture absorbing material of the hood-like element is adapted to support absorption of moisture including mucus and/or stomal output during the time it takes to exchange the ostomy appliance. In embodiments, the absorption capacity is adapted to allow for absorption for up to 60 minutes. Since every stoma exhibits its own individual pattern in terms of exuding moisture, mucus and output, the required mass or volume of moisture absorbing material necessary to meet a certain absorption time requirement, e.g. up to 60 minutes, can be based on empirical data/experience. In one embodiment, the absorption capacity is configured to allow for absorption for about 10 minutes.

In embodiments, an inside of the hood-like element is configured to additionally include or define a collecting volume to support temporary collection of stomal output for a short period, for example about 10 minutes. This is particularly, but not exclusively, useful for stoma covers for colostomies exuding more solid stomal output.

In embodiments, the moisture absorption material of the hood-like element is adapted to expand into a collecting volume inside the hood-like element, thereby filling the collecting volume wholly or partly by such expansion, upon absorption of moisture from the mucus membrane of the stoma and/or from the fluid components of the stomal output.

In embodiments, the moisture absorption material of the hood-like element is adapted to provide a lining of the inside of the hood-like element. In such embodiments, an inner surface of the hood-like element is provided as a layer of the moisture absorption material. In embodiments, the lining of the moisture absorption material forms an entirety of the inner surface of the hood-like element.

In embodiments, the moisture absorption material of the hood-like element is provided towards the distal end portion at the inside of the hood-like element. This is to be understood such that the moisture absorption material is provided closer to the distal end portion than to the proximal end portion of the inside of the hood-like element. In embodiments, the moisture absorption material of the hood-like element is provided at the closed end portion inside the hood-like element.

In embodiments, the moisture absorption capacity of the moisture absorbing material of the hood-like element is adapted to be in a range of 0-100 ml. Thereby, adequate moisture absorption capacity of the stoma cover to function as a temporary stoma cover during exchange of an ostomy appliance is ensured. The moisture absorption capacity can be varied according to stoma type and size. Further, any attributes of an individual user, such as diet and/or diseases or disorders, can play a role when deciding on the moisture absorption capacity of the temporary stoma cover. In one embodiment, the moisture absorption capacity is configured to be in a range of 5-15 ml, such as about 10 ml.

In embodiments, a longitudinal length of the hood-like element between a proximal-most end and a distal-most end thereof, is adapted to be between 30 and 70 mm. This helps provide for easy handling of the stoma cover and ensures sufficient temporary functioning capacity for the stoma cover during exchange of an ostomy appliance. In rare cases, stomas protrude significantly from the skin surface of the user. It is understood that the length of the hood-like element can be extended by design to be longer than 70 mm, if need be.

In embodiments, the applicator of the system includes a first end portion and a second end portion and defines an internal lumen between the first end portion and the second end portion.

In embodiments, the applicator of the system includes an oblong element having a first end portion and a second end portion. The oblong element defines an internal lumen between the first end portion and the second end portion. In embodiments, the oblong element is a tubular element. In this disclosure, the phrase "oblong" is to be understood as a shape that is longer than it is wide. Further, "lumen" is to be understood as a cavity or passage inside and through the oblong or tubular element.

In embodiments, the second end portion of the oblong element applicator is configured to receive and hold the proximal end portion of the hood-like element in expanded disposition.

In embodiments, the second end portion of the oblong element is configured to be wider than the first end portion of the oblong element. The second end portion of the oblong element is configured to receive and hold the proximal end portion of the hood-like element of the stoma cover in the expanded disposition.

In embodiments, a major portion of the hood-like element is received or located in the internal lumen defined by a wall of the oblong element extending between the first end portion and the second end portion, when the proximal end portion of the hood-like element is held in the expanded disposition by the second end portion of the applicator. In embodiments, the distal end portion of the hood-like element is configured to extend toward the first end portion of the applicator inside the internal lumen of the applicator.

In embodiments, at least an external shape of the applicator corresponds to the shape of a truncated pyramid. In other embodiments, at least the external shape of the applicator corresponds to the shape of a conical element or cone, tapering along at least a portion of a sidewall from the first end portion to the second end portion of the applicator. In embodiments, an internal shape of the applicator mirrors the external shape and corresponds to ("follows") the external shape of the applicator. In one example, both the external shape and the internal shape of the applicator has the shape of a truncated pyramid.

In embodiments, the applicator comprises a paper-based material. In embodiments, the applicator consists of a paper-based material.

In embodiments, the applicator comprises a paperboard material.

According to Wikipedia, paperboard is a thick paper-based material. While there is no rigid differentiation between paper and paperboard, paperboard is generally thicker (usually over 0.30 mm) than paper. In some definitions, paperboard is paper with a grammage above 250 g/m2, but there are exceptions. Paperboard can be single- or multi-ply. The definition of paperboard is intended to include materials commonly understood to be "cardboard", however "cardboard" may not be generally accepted as a clear or specific definition.

In embodiments, the applicator is configured to be deformable by finger-pressure to release the proximal end portion of the hood-like element from the hold in the expanded disposition, to make the hood-like element releasable from the applicator. In embodiments, only a portion of the applicator, such as the second end portion of the applicator holding the proximal end portion of the hood-like element in the expanded disposition, is deformable. In embodiments, the applicator comprises or consists of a paper-based material, which is useful in providing for the applicator to be deformable by finger-pressure in a particularly effective manner.

In embodiments of the system, wherein the applicator is configured from a paper-based material, such as including paperboard (or "cardboard"), and further is configured to be deformable by finger-pressure, the system provides a particularly useful, easily handled and intuitive solution for handling and applying a temporary stoma cover over a stoma of a user during exchange of an ostomy appliance.

In embodiments, the applicator comprises a groove or slot in a portion of a sidewall of the applicator. The groove or slot is configured to receive and allow a pulling strip provided of the hood-like element to extend therethrough. This facilitates gripping and hence pulling on the pulling strip at an external surface of the sidewall (external surface) of the applicator. Thereby, initial and/or continuous adjustment of the size of the stoma entrance to create a snug fit of the stoma cover around the stoma. This is possible also with the stoma cover being received/positioned in the applicator. Thus, the system of the disclosure provides additional control in terms of applying the stoma cover. In embodiments, the groove or slot is provided at the second end portion of the oblong element of the applicator. In embodiments, the groove or slot is provided at the second end portion of the oblong element of the applicator and the pulling strip provided at the adjustable proximal end portion of the hood-like element extends through the groove or slot.

In another aspect, the disclosure relates to a stoma cover including a hood-like element having a proximal end portion and a distal end portion. The hood-like element defines a generally longitudinal direction between the first and the second end portions, and the proximal end portion of the hood-like element is configured to be adjustable at least in a direction transverse to the longitudinal direction. This provides for a stoma entrance of the stoma cover to be of variable size. The distal end portion of the hood-like element is configured as a closed end portion. The proximal end portion of the hood-like element provides for a first size of the stoma entrance in an expanded disposition to be bigger than a second size of the stoma entrance in a non-expanded disposition. Advantages and effects of the stoma cover according to the disclosure are similar to and/or include those described above in relation to the first aspect of the disclosure.

In embodiments, the adjustable proximal end portion of the hood-like element of the stoma cover according to the second aspect of the disclosure includes a resilient component. In embodiments, the resilient component includes a stretchable component including an elastic thread, strip and/or band.

In embodiments of the second aspect, the adjustable proximal end portion of the hood-like element includes a pulling strip configured to reduce a size of a stoma entrance in the stoma cover, when the pulling strip is pulled.

In yet another aspect, the disclosure relates to a kit of parts including the system according to the first aspect of the disclosure, and a packaging. In embodiments, the packaging itself includes one or more of a paper-based and a polymer-based material.

In embodiments, the kit of parts includes a set of instructions for use provided with the packaging. The set of instructions for use explains the functionality of the system and how to use and handle its components to apply the stoma cover of the system over a stoma using the applicator of the system in an intended and correct manner.

In embodiments, the kit of parts includes a plurality of stoma covers and a corresponding plurality of applicators. Thereby, many single-use stoma covers and applicators can be provided to a user for use at each exchange of the ostomy appliance, which happens frequently, for some users several times each day.

In embodiments, the (plurality of) applicator(s) and the stoma cover(s) of the kit of parts are provided being separated from each other in the packaging (i.e. not engaged with each other "beforehand" or "at manufacture"). In other embodiments, the hood-like element of the stoma cover is inserted into and received by the applicator at manufacture and the system is delivered to the user with its components in engaged relationship. In embodiments, each of the applicators—with or without a hood-like element engaged thereto—can be manipulated to be substantially of flat shape and thus allow for plural systems according to the disclosure to be packaged within a single packaging of the kit of parts, because each applicator and stoma cover thereby individually takes up less volume in the packaging. Particularly, but not exclusively, this "flat packaging" is advantageously achieved when the applicator takes the shape of an oblong element, provided with a truncated pyramid external (and/or internal) shape and is made from a paper-based material.

Advantages and effects of the kit of parts according to the disclosure include those described above in relation to the first aspect of the disclosure.

DETAILED DESCRIPTION OF THE DRAWINGS

FIG. 1 is a schematic, perspective view of a system 15 for applying a stoma cover over a stoma of a user including a releasable stoma cover 20 and a manipulable applicator 22 held by one hand of a user. FIG. 1 further illustrates how the releasable stoma cover 20 is received and held by the applicator 22 in a position ready for being applied over a stoma of the user (not shown).

Figure 2A:
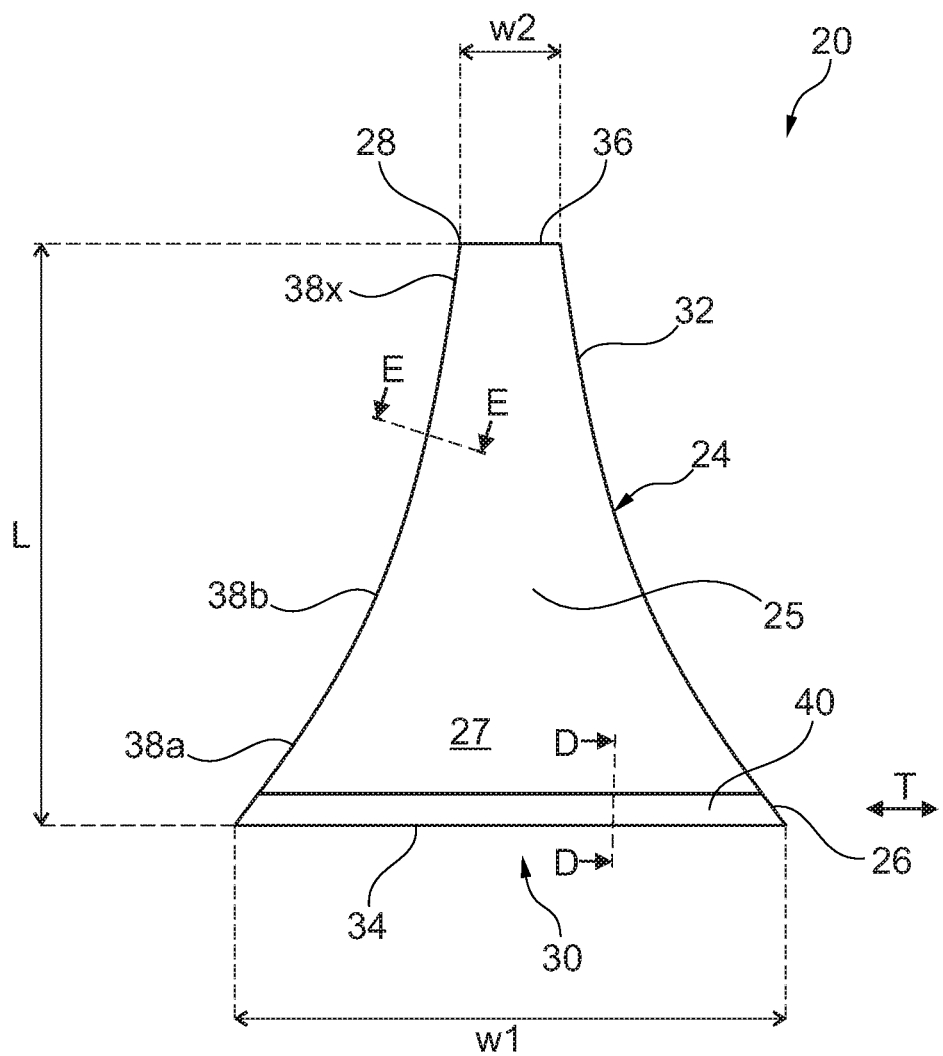
FIG. 2A is a cross-sectional side view of one embodiment of a releasable stoma cover of the system of the disclosure.

FIG. 2A is a cross-sectional side view of one embodiment of a releasable stoma cover 20 of the system 15 of the disclosure including a hood-like element 24. In FIG. 2A, the stoma cover 20 is not engaged with the applicator 22 of the system 15. Also, the stoma cover 20 is not illustrated applied over a stoma of a user.

The releasable stoma cover 20 includes a hood-like element 24 including an adjustable proximal end portion 26 and a distal end portion 28. The releasable stoma cover defines a generally longitudinal direction L between the first and the second end portions 26, 28. A stoma entrance 30 of the stoma cover 20 is of variable size because the adjustable proximal end portion 26 of the hood-like element 24 is configured to be adjustable at least in a direction T transverse to the longitudinal direction L. The distal end portion 28 of the hood-like element 24 is configured as a closed end portion. FIG. 2A further illustrates embodiments wherein the hood-like element 24 is provided with a collecting volume 25 at an inside 27 of the hood-like element 24 for short-term or temporary collecting of stomal output and/or moisture. In the FIG. 2A embodiment, the adjustable proximal end portion 26 of the hood-like element 24 is adapted to be adjustable by including a resilient component 40.

In the embodiment of FIG. 2A, the hood-like element 24 is provided with a generally conical shape and forms a sidewall 32, such as an annular sidewall, wherein the annular sidewall 32 in the cross-sectional view tapers from a first smaller width w1 of the hood-like element 24 at a distal-most end 36 thereof, to a greater width w2 at a proximal-most end 34 of the hood-like element 24. In the embodiment of FIG. 2A, the tapering sidewall 32 of the hood-like element 24 is adapted to be gradually tapering, being made to include a plurality of connected and stepwise provided portions including portions 38a, 38b, . . . , 38x. In other words, the sidewall 32 in the FIG. 2A embodiment does not taper at a constant rate or coefficient. In the embodiment of FIG. 2A, a distal-most portion 38x of the sidewall 32 includes the distal-most end 36 of the hood-like element 24 and forms the closed end portion.

In the embodiment of FIG. 2A, the adjustable proximal end portion 26 of the hood-like element 24 includes a resilient component 40, which provides for the first size S1 (FIG. 2B) of the stoma entrance 30 in the expanded disposition of the proximal end portion 26 of the hood-like element 24 to be stretched and be bigger than the second size S2 (FIG. 2C) of the stoma entrance 30 in a non-expanded disposition, i.e. S2>S1. In the embodiments represented by FIG. 2A, the resilient component 40 is integrated in the sidewall 32 of the hood-like element 24 at the adjustable proximal end portion 26 thereof.

Figure 2C:
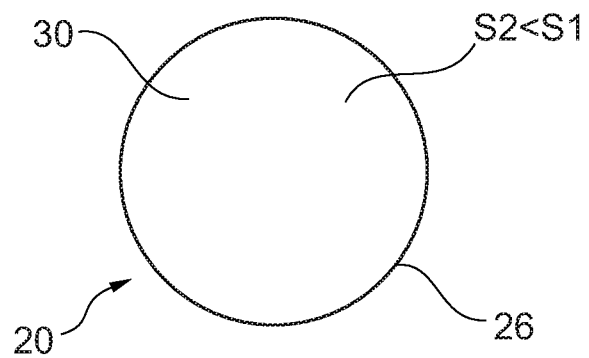
FIG. 2C is a schematic bottom view of one embodiment of a stoma cover of the disclosure showing a stoma entrance in a proximal end portion thereof in a non-expanded disposition.
Figure 2B:
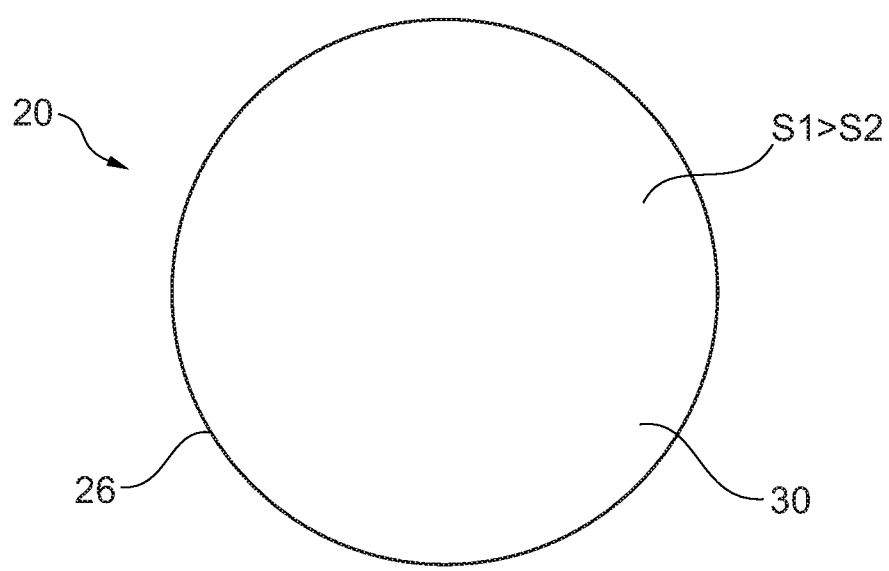
FIG. 2B is a schematic bottom view of one embodiment of a stoma cover of the disclosure showing a stoma entrance in a proximal end portion thereof in an expanded disposition.

FIGS. 2B and 2C are schematic bottom views of the stoma entrance 30 in the adjustable proximal end portion 26 of the stoma cover 20. In FIG. 2B, a first size S1 of the stoma entrance 30 formed at the adjustable proximal end portion 26 of the hood-like element 24 is of larger (bigger) size, than a second (relatively smaller) size of the stoma entrance present, when the adjustable proximal end portion 26 of the hood-like element 24 is in a non-expanded disposition, as illustrated in the view of FIG. 2C showing the stoma entrance 30 at the adjustable proximal end portion 26 of the stoma cover 20.

Figure 2D:
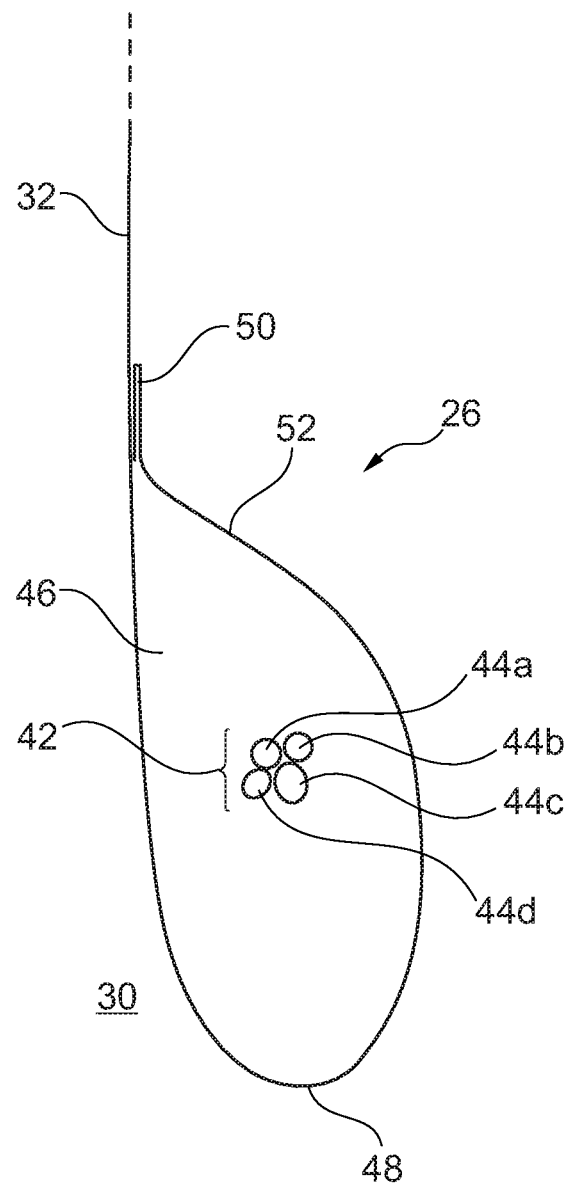
FIG. 2D is a cross-sectional view taken along line D-D in FIG. 2A showing in enlarged view a cross-section of a portion of a proximal end portion of one embodiment of a hood-like element of the system including a resilient component.

FIG. 2D is a cross-sectional view taken along line D-D in FIG. 2A and shows in enlarged view a cross-section of a portion of the adjustable proximal end portion 26 of one embodiment of the hood-like element 24. In the embodiment of FIG. 2D, the resilient component 40 comprises an elastic thread 42 including four filaments 44a-44d provided in a side-by-side relationship with each other. In embodiments, the resilient component 40 includes an elastic band.

In the embodiment of FIG. 2D, the adjustable proximal end portion 26 of the hood-like element 24 is configured to include a pocket 46 in which the elastic thread 42 is located to form the resilient component 40 of the hood-like element 24. The elastic thread 42 is here shown to be loosely provided inside the pocket 46. The pocket 46 is provided at (or including) a peripheral edge 48 of the adjustable proximal end portion 26 forming part of an edge or edge area of the stoma entrance 30 of the stoma cover 20.

Further, in the embodiment of FIG. 2D, the pocket 46 is shown formed by folding over the adjustable proximal end portion 26 of the hood-like element 24 and attaching the folded-over portion to the sidewall 32 of the hood-like element 24, e.g. at a weld 50. The portion 52 of the adjustable proximal end portion 26 surrounding or forming the pocket 46 can alternatively or additionally be made from an elastic material, such as an elastic layer or an elastic band, to provide the adjustable proximal end portion 26, in this embodiment including a resilient component.

Figure 2E:
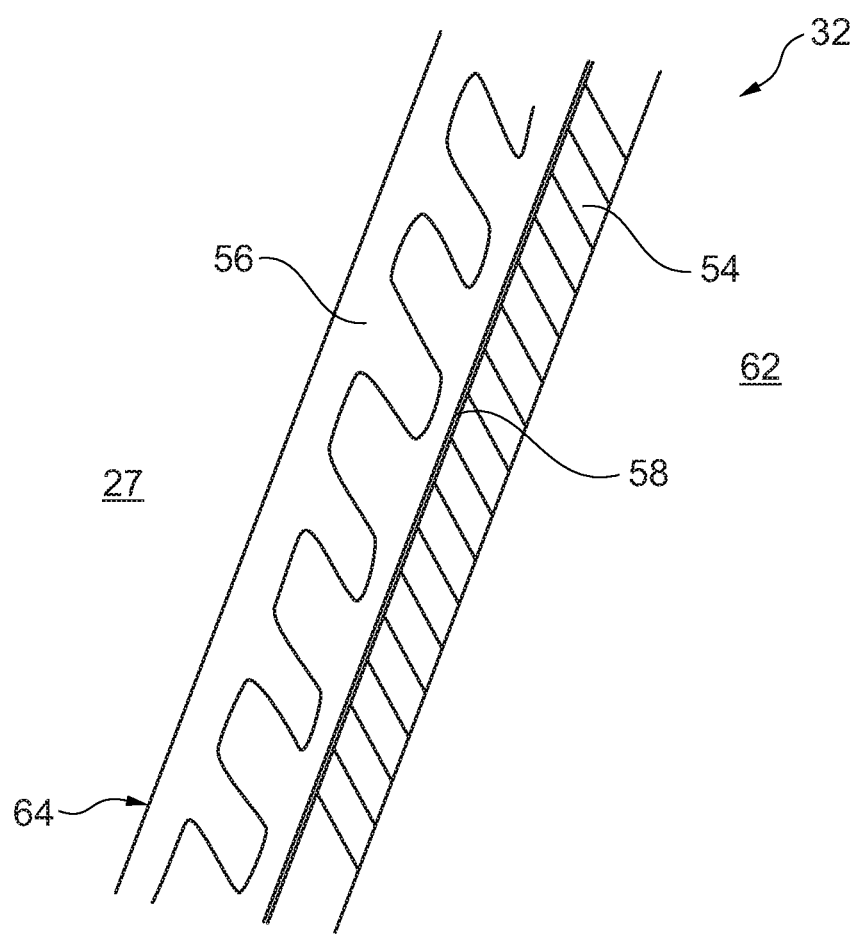
FIG. 2E is a cross-sectional view taken along line E-E in FIG. 2A and shows in enlarged view a cross-section of a portion of a sidewall of one embodiment of a hood-like element of the system of the disclosure.

FIG. 2E is a cross-sectional view taken along line E-E in FIG. 2A and shows in enlarged view a cross-section of a portion of the sidewall 32 of one embodiment of the hood-like element 24. In the embodiment of FIG. 2E, the sidewall 32 of the hood-like element 24 includes a non-woven material 54, an absorbing material 56 and a moisture impermeable material 58. In the embodiment of FIG. 2E, the materials 54, 56, 58 are provided in layers and in a "layered" relationship with each other, and combine to form the sidewall 32 of the hood-like element 24. The moisture impermeable material layer 58 is provided as a middle layer between the non-woven material layer 54 and the moisture absorption layer 56. In the embodiment of FIG. 2E, the non-woven material layer 54 is adapted to form an outer layer of the sidewall 32 of the hood-like element 24, facing (exposed to) the external surroundings 60 of the hood-like element 24, and the moisture absorption material layer 56 forms an inner layer of the sidewall 32 of the hood-like element 24 facing (exposed to) an inside 27 of the hood-like element 24.

In the FIG. 2E embodiment, the moisture absorption material layer 56 of the hood-like element 24 is adapted to expand into the collecting volume 25 of the inside 27 (FIG. 2A) of the hood-like element 24, and fill the collecting volume 25 wholly or partly upon absorption of moisture from stomal output or mucus. In the embodiment of FIG. 2E, the moisture absorption material layer 56 can be understood to be adapted to provide a lining 64 of the inside 27 of the hood-like element 24.

Figure 3:
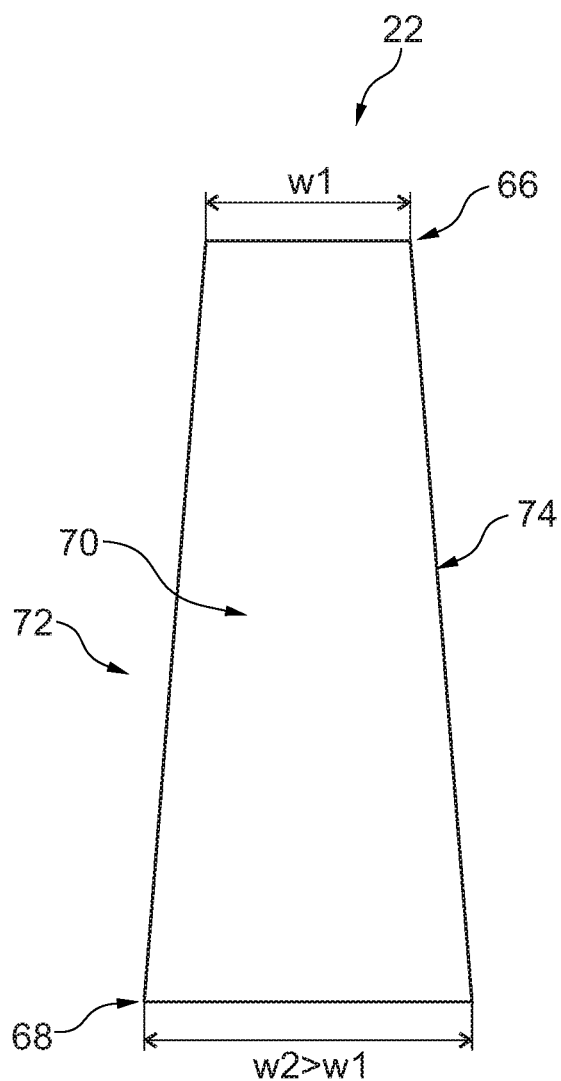
FIG. 3 is a schematic, cross-sectional side view of one embodiment of an applicator of the system of the disclosure.

FIG. 3 is a cross-sectional side view of one embodiment of an applicator 22 of the system 15. The applicator 22 includes a first end portion 66 and a second end portion 68 and defines an internal lumen 70 between the first end portion 66 and the second end portion 68.

In the embodiments represented by FIG. 3, the applicator 22 of the system is an oblong element 72 having a first end portion 66 and a second end portion 68. The oblong element 72 defines an internal lumen 70 extending between the first end portion 66 and the second end portion 68. In embodiments, the second end portion 68 of the oblong element 72 receives and holds the adjustable proximal end portion 26 of the hood-like element 24 (not shown in FIG. 3) in the expanded disposition. The second end portion 68 of the oblong element 72 is configured to be wider than the first end portion 66 of the oblong element, represented by w2>w1.

In embodiments, including those of FIG. 3, an external shape of the applicator 22 takes the shape of a truncated pyramid. The 'truncated pyramid' external shape of the applicator 22 is shown to include a tapering wall 74 between the first end portion 66 and the second end portion 68 of the applicator 22. Also, an internal shape of the applicator 22 mirrors the external shape and has the shape of a truncated pyramid in the illustrated embodiment.

Figure 4:
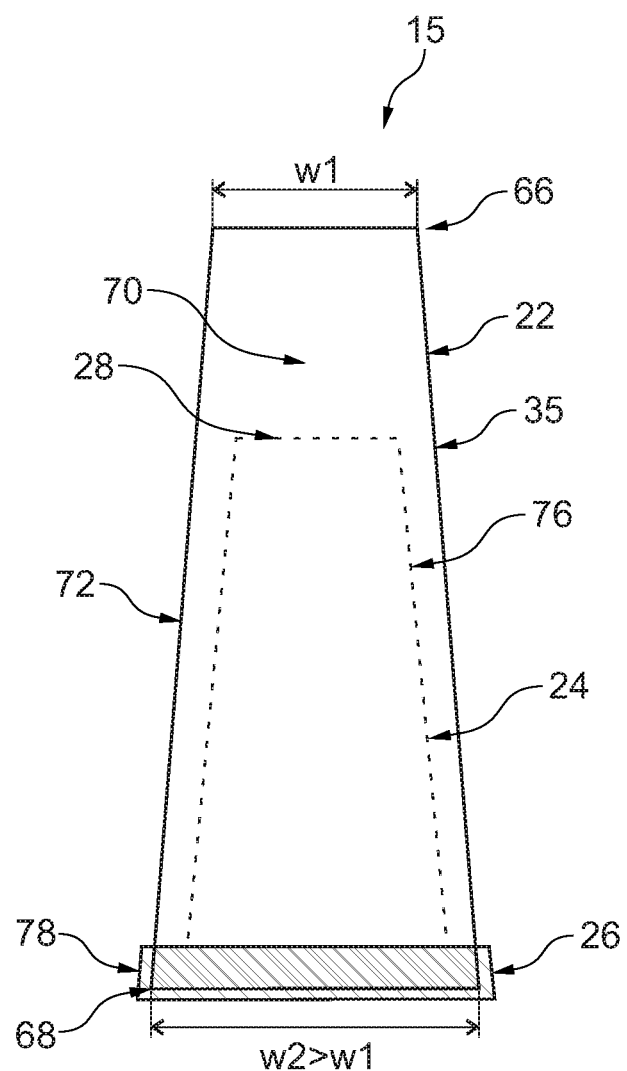
FIG. 4 is a schematic, cross-sectional side view of one embodiment of the applicator of FIG. 3 receiving the stoma cover of the system therein.

In embodiments, as illustrated in FIG. 4, a longitudinal portion 76 of the hood-like element 24 is received or located in the internal lumen 70 defined by a wall 35 of the oblong element 72. The longitudinal portion 76 of the hood-like element 24 inside the internal lumen 70 is shown with a punctured line to illustrate that it is positioned inside the applicator 22. The distal end portion 28 of the hood-like element 24 extends toward the first end portion 66 of the applicator 22 inside the internal lumen 70 of the applicator 22. The wall 35 of the applicator 22 extends between the first end portion 66 and the second end portion 68, and the adjustable proximal end portion 26 of the hood-like element 24 is held stretched-out in the expanded disposition by the second end portion 68 of the applicator 22. The adjustable proximal end portion 26 of the hood-like element 24 is folded in fold 78 over the second end portion 68 of the applicator 22. The fold 78 is folded such that an external surface of the adjustable proximal end portion 26 of the hood-like element 24 engages with an external surface of the wall 32 of the applicator 22 at the second end portion 68 thereof. The fold 78 is illustrated in the figure by a hatched area. The second end portion 68 of the oblong element 72 of the applicator 22 is shown in fully drawn line for illustration purposes, however it is to be understood that fold 78 of the adjustable proximal end portion 26 of the hood-like element 24 covers the edge of the second end of the applicator 22 in this configuration.

In the embodiments of FIGS. 3 and 4, the applicator 22 can be deformed by finger-pressure to release the proximal end portion 26 of the hood-like element 24 from the stretched-out hold in the expanded disposition. This aids in releasing the "entire" hood-like element 24 from the applicator 22. The illustrated applicator 22 can advantageously be made from a paper-based material to be deformable by finger-pressure.

FIGS. 5-12 are schematic perspective illustrations showing embodiments of the system 15 of the disclosure and explaining one exemplary procedure of using the applicator 22 to apply embodiments of the hood-like element 24 of the stoma cover 20 of the system 15 of the disclosure including a resilient component, including steps of preparing and handling the peristomal skin of the user.

Figure 5:
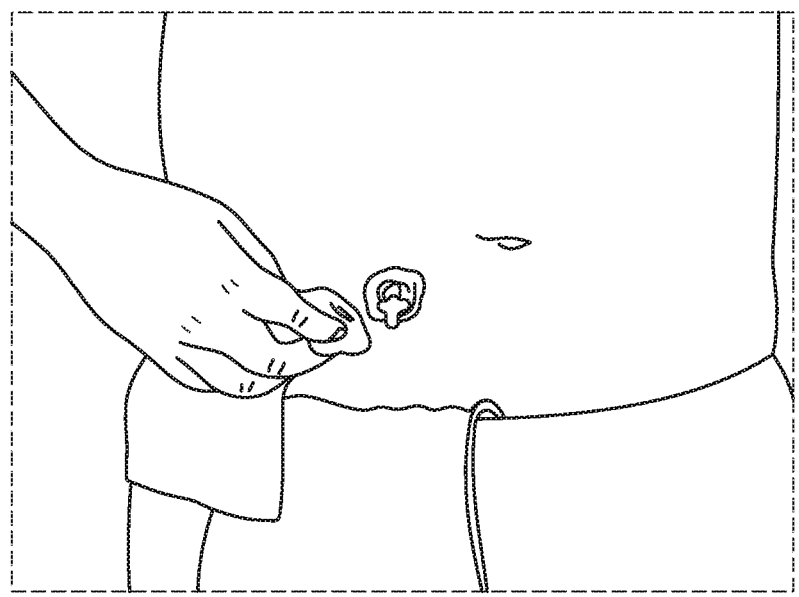
FIGS. 5-12 are schematic perspective illustrations showing embodiments of the system of the disclosure and explaining one exemplary procedure of using the applicator to apply a hood-like element of the stoma cover including a resilient component.

FIG. 5 illustrates a situation where a user has removed the used ostomy appliance from the skin surface, and is cleaning the peristomal skin area around the stoma with a paper tissue, rag or like prepare the peristomal skin area for application of a fresh ostomy appliance. The figures also show an exemplary protective sheet (not forming part of the claimed subject matter of the disclosure) held in place over an edge of the waist lining of the user's pants.

Figure 6:
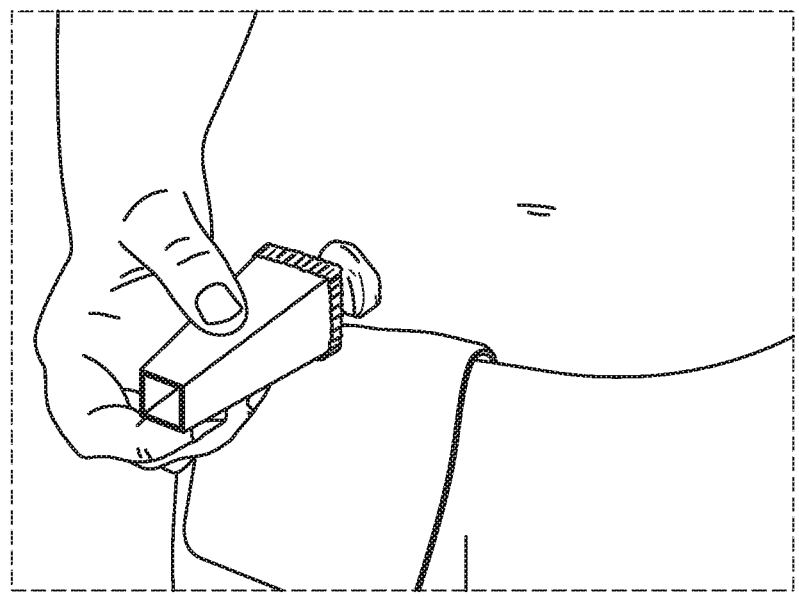

FIG. 6 illustrates a situation where the peristomal skin area has been cleaned, and the user is holding the applicator 22 with the stoma cover 20 including the resilient component 40 of the system received inside an internal lumen, and held by the applicator in a position ready to apply the stoma cover 20 over the stoma. The applicator 20 makes it simple and easy for the user to gently and accurately apply the stoma cover 20 including the resilient component 40 over the stoma.

Figure 7:
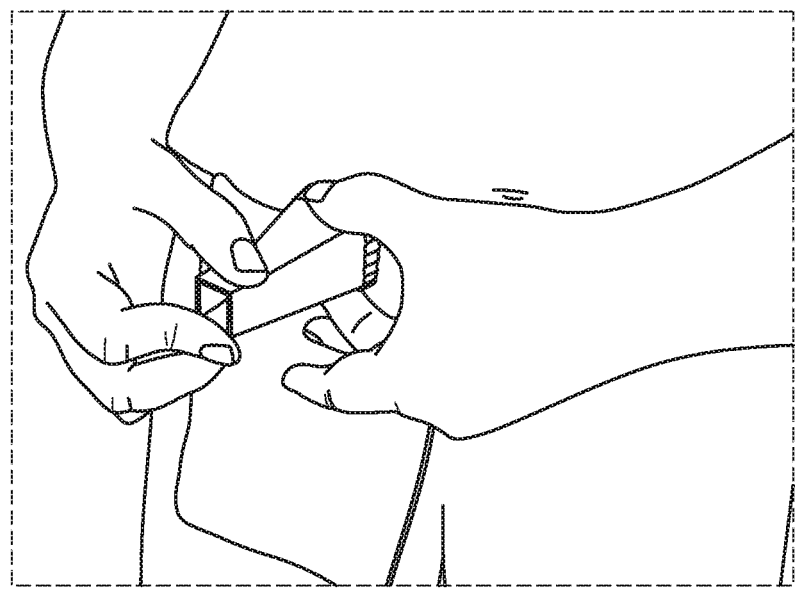

FIG. 7 illustrates how the user may apply finger-pressure to one or more locations on an outside of the applicator 22. Particularly, in FIG. 7, the user applies finger-pressure at the first end portion 66 and at the second end portion 68 (FIGS. 3-4) of the applicator 22. When applying finger-pressure at the second end portion 68 of the applicator 22, the user simultaneously controls the adjustable proximal end portion 26 of the hood-like element 24 provided as a fold 78 folded around an edge of the second end portion 68 of the applicator 22 and including resilient component 40.

Figure 8:
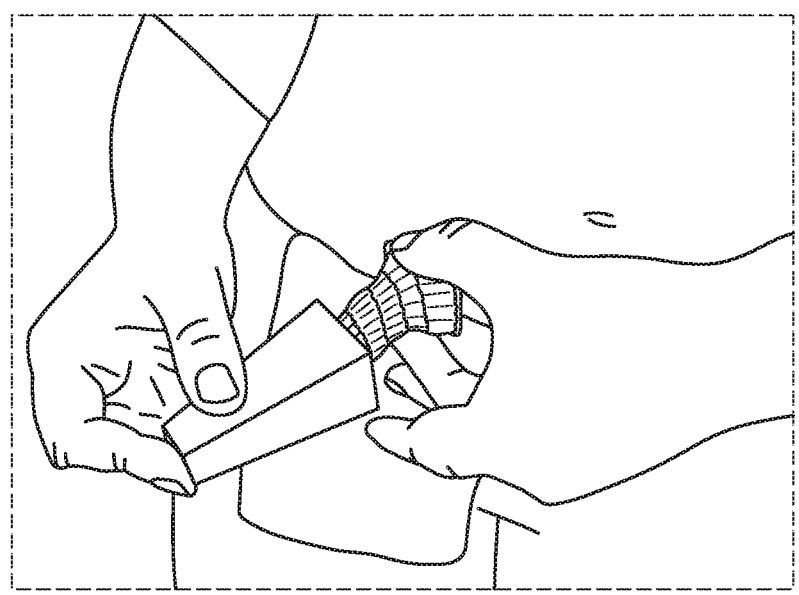

FIG. 8 illustrates a situation where the stoma cover 20 is released from the applicator 22 to be applied over the stoma. The applicator 22 is being removed by the user and can for example be discarded. The stoma cover 20 is now being located over the stoma. FIG. 8 shows how the user may help control the application of the stoma cover 20 with the fingers of one hand, while the applicator 22 is being removed and discarded with the other hand.

Figure 9:
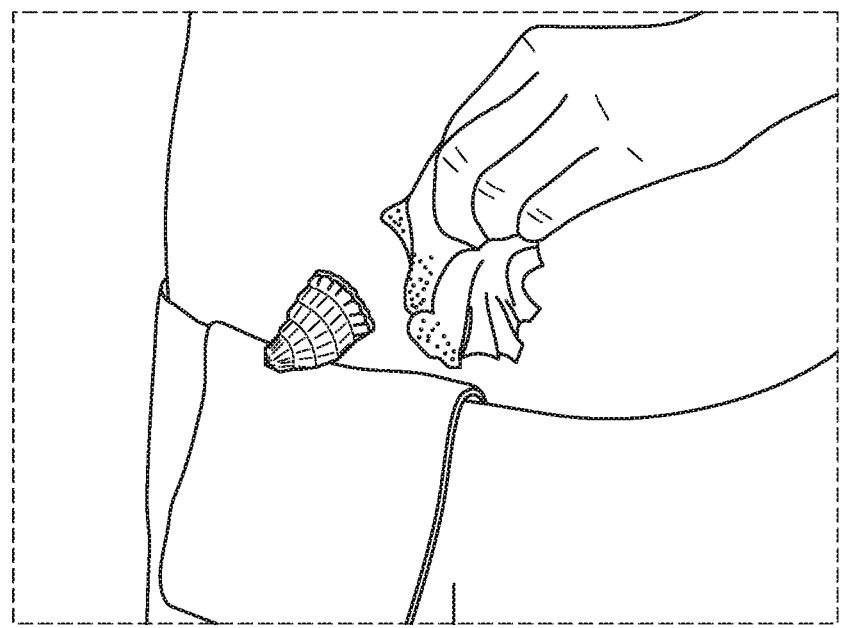

FIG. 9 illustrates how the stoma cover including the resilient component is now in place over the stoma, and the user may perform any further required cleaning action in the peristomal skin area.

Figure 10:
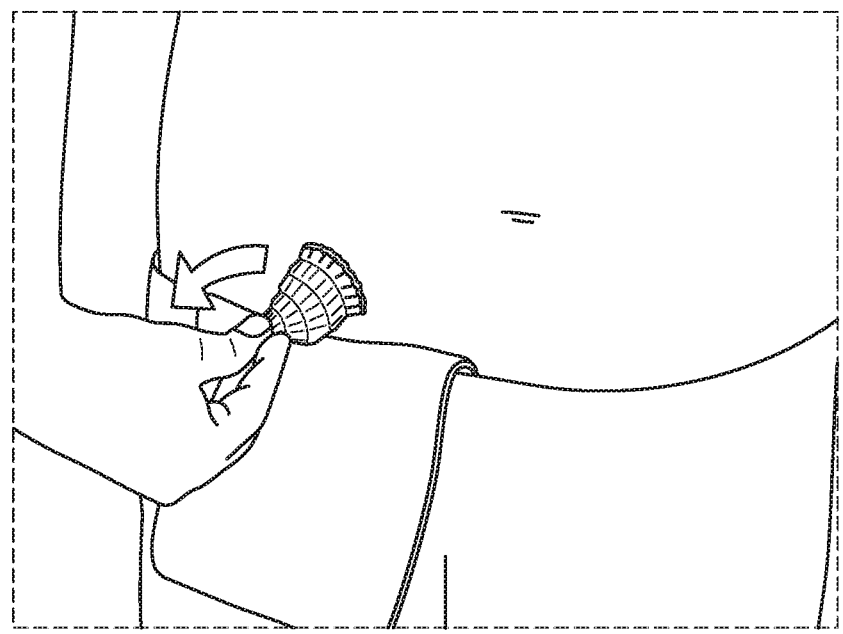

FIG. 10 illustrates how the stoma cover including the resilient component can be removed ("taken off") the stoma by the user, after the cleaning action of the peristomal area has been completed.

Figure 11:
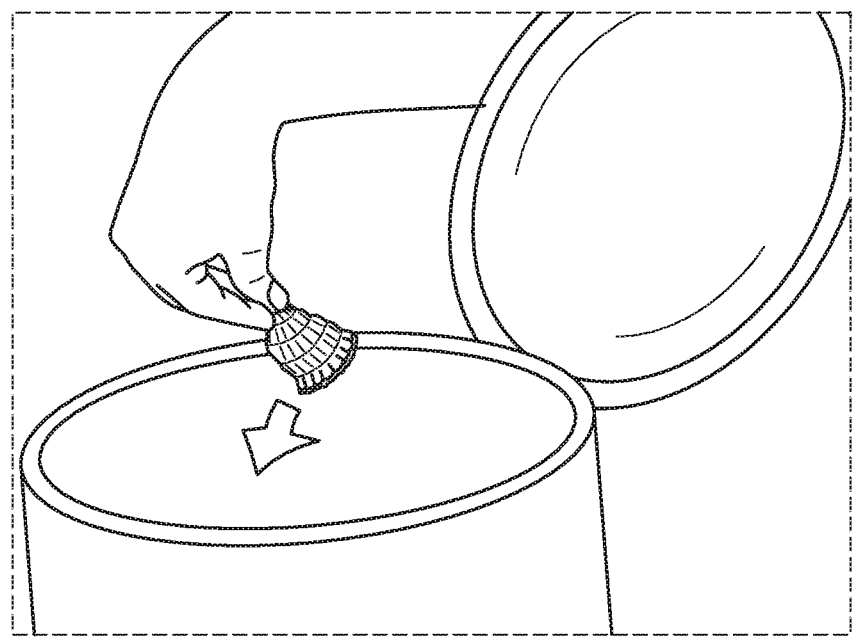

FIG. 11 illustrates how the stoma cover 20, including a resilient component and having been used for a temporary covering of the stoma during exchange of the ostomy appliance, is discarded, underlining how in such embodiments the stoma cover is adapted to be a single-use device or element.

Figure 12:
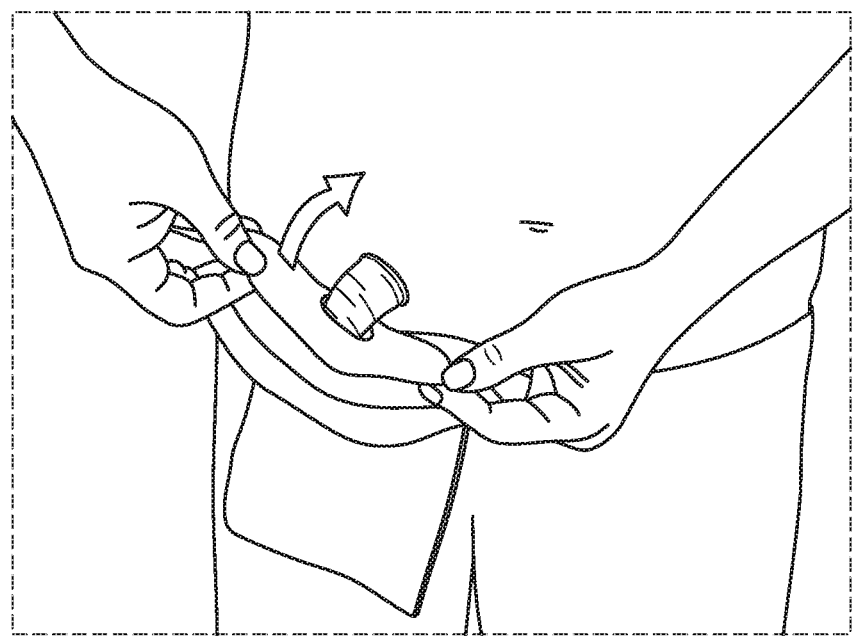

FIG. 12 illustrates a situation where the user attaches a fresh ostomy appliance to the stoma without any contamination or soiling from stomal output on the peristomal skin area, because of the use of the system including the applicator and embodiments of the stoma cover including a resilient component. This provides an improved security against leakage or adhesive failure of the fresh ostomy appliance prematurely, i.e. helps to prevent that the ostomy appliance must be exchanged before its full capacity (or 'end of life') has been reached. This in turn saves the number of required ostomy appliance exchanges to the benefit of the user and lowering the costs involved with the generally chronic condition of having a stoma.

Figure 13:
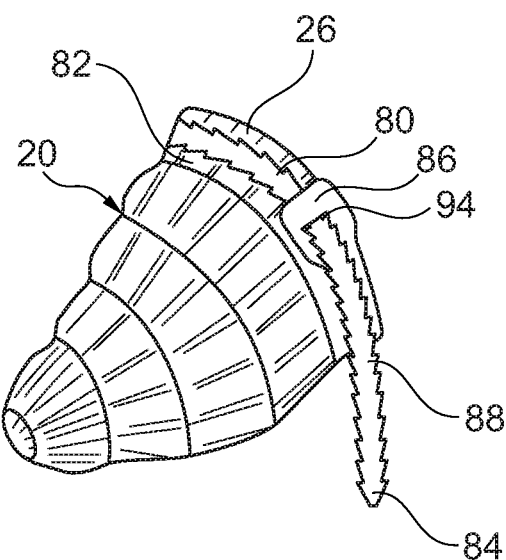
FIG. 13 is a perspective view of one embodiment of a releasable stoma cover of the system including a flushable hood-like element.

FIG. 13 is a perspective view of one embodiment of a releasable stoma cover 20 of the system 15 of the disclosure including a flushable hood-like element 24. The stoma cover 20 is not engaged with the applicator 22 of the system 15. Also, the flushable hood-like element 24 of the stoma cover 20 is illustrated un-applied over a stoma of a user.

In the embodiment of FIG. 13, the adjustable proximal end portion 26 of the flushable hood-like element 24 includes a pulling strip 80, which facilitates a reduction of the size of the stoma entrance (not visible) of the adjustable proximal end portion 26 of the flushable hood-like element 24. Upon a pull on the pulling strip 80, the size of the stoma entrance decreases. In embodiments represented by FIG. 13, the pulling strip 80 is provided on an external surface 82 of the flushable hood-like element 24 at the adjustable proximal end portion 26 thereof. The pulling strip 80 is configured to reduce the size of the stoma entrance when a free end 84 of the pulling strip 80 is pulled. The pulling strip 80 is configured to form a noose or snare or loop-like portion, such that a pull exerted on the free end 84 of the pulling strip 80 causes a tightening of the noose- or snare-like portion, and thereby reduction of the size of the stoma entrance of the flushable hood-like element 24.

Figure 14:
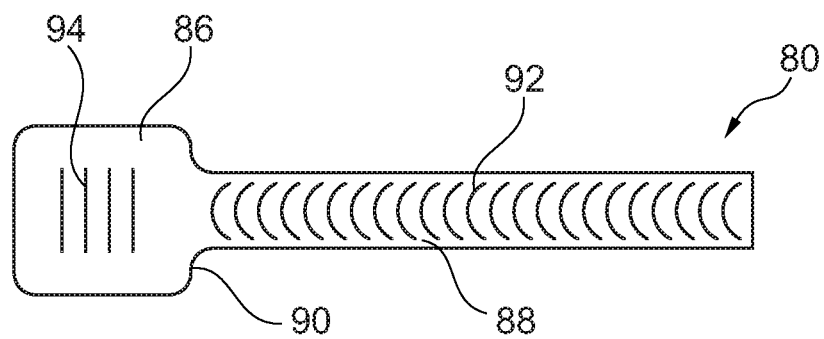
FIGS. 14 and 15 are planar views of embodiments of a pulling strip of an adjustable proximal end portion of a stoma cover of the system including a flushable hood-like element.
Figure 15:
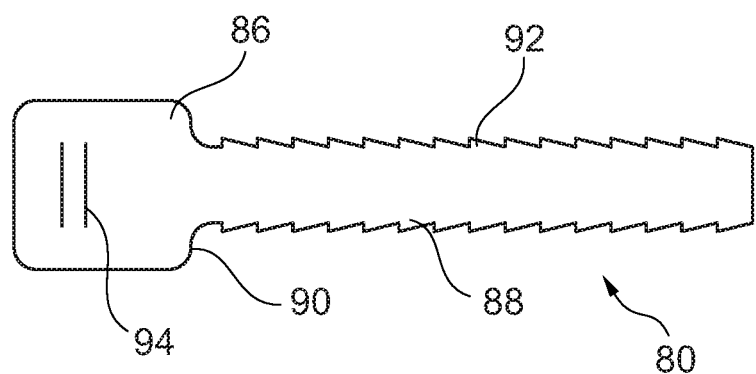

FIGS. 14 and 15 are planar views of embodiments of a pulling strip 80, wherein the pulling strip 80 is configured to prevent the size of the stoma entrance from re-expanding. The pulling strip 80 includes a buckle portion 86 and a strap portion 88 extending from a first side 90 of the buckle portion 86. The strap portion 88 has a longitudinal extent that is larger than a largest dimension of the buckle portion 86. In the embodiments of FIG. 15, the strap portion 88 includes a plurality of barbs or saw tooth-like projections 92 configured to combine with a through-going slit or opening 94 provided in the buckle portion 86. In the embodiments of FIG. 15, the barbs or saw tooth-like projections 92 extend from an edge of the strap portion 88. In the embodiments of FIG. 14, the barbs 92 extend from a planar surface 96 of the strap portion 88 and include semi-circular projections (in the planar view of FIG. 14, the projections 92 should be understood as extending into or out of the plane of the paper). The slit or opening 94 is dimensioned to allow the strap portion 88 to pass through it, but also to prevent the strap portion 88 from exiting backwards out of the slit 94. The strap portion 88 is adapted to provide for the pulling strip 80 to extend around the root of the stoma and pass through the slit 94 in the buckle portion 86. Only allowing for the barbs or saw tooth-like projections 92 to pass one-way through the slit or opening 94, prevents the noose-like portion of the pulling strip 80 from re-expanding, and thus in turn prevents the size of the stoma entrance 30 from increasing again once it has been decreased.

Figure 16:
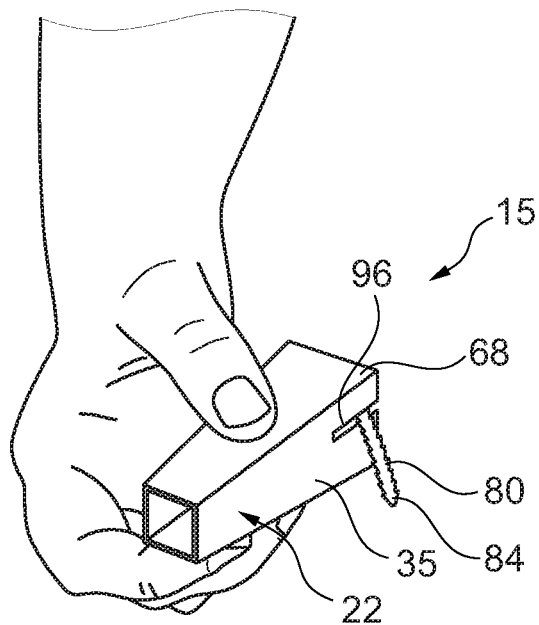
FIG. 16 is a schematic, perspective view of one embodiment of a system for applying a flushable hood-like element of a stoma cover.

FIG. 16 is a schematic, perspective view of a system 15 for applying a flushable hood-like element 24 of a stoma cover over a stoma of a user in which the releasable stoma cover 20 is located inside (and therefore not visible) a manipulable applicator 22 held by one hand of a user.

FIG. 16 further illustrates how the applicator 22 includes a slot 96 in a portion of a wall 35 of the applicator 22. The slot 96 is configured to receive and allow a pulling strip 88 provided on the flushable hood-like element 24 to extend therethrough. This facilitates gripping and pulling on a free end 84 of the pulling strip 80 external of the wall 35 of the applicator 22. Thereby, it is possible to adjust a size of the stoma entrance 30 in the stoma cover 20 and to create a snug fit of the stoma cover 20 around the stoma also before release of the stoma cover 20 from the applicator 22. In the FIG. 16 embodiment, the slot 96 is provided at the second end portion 68 of an oblong element of the applicator 22. With the slot 96 provided at the second end portion 68 of the oblong element of the applicator 22, and with the pulling strip 80 provided at the adjustable proximal end portion 26 of the flushable hood-like element 24 (inside the applicator 22), the pulling strip 80 advantageously extends through the slot 96 to allow for adjustment of the size of the stoma entrance 30 of the stoma cover 20.

Figure 17:
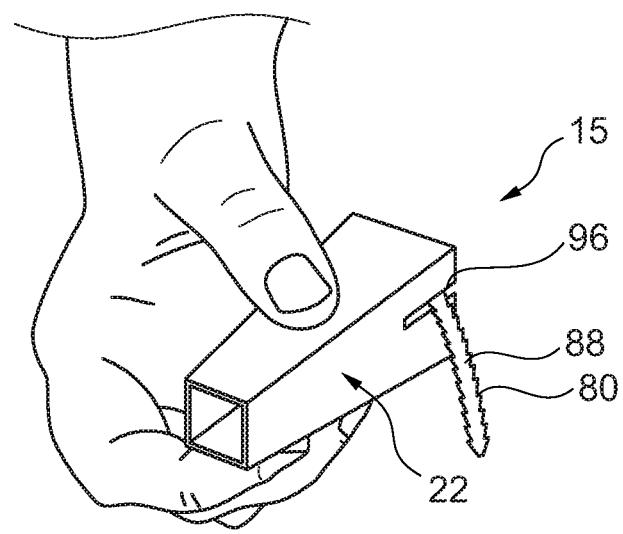
FIG. 17 is a schematic, perspective view of one embodiment of the system of FIG. 16 further illustrating a pulling strip in a position where the pulling strip is pulled through a slot of the applicator.

FIG. 17 is a schematic, perspective view of the system of FIG. 16 illustrating the pulling strip 80 in a position where it has been pulled through the slot 96 of the applicator 22, such that a greater portion of the strap portion 88 of the pulling strip 80 extends externally to the applicator 22. Thereby, the size of the stoma entrance 30 of the flushable hood-like element 24 of the stoma cover 20 is reduced to work the stoma cover 20 into a snug fit around the stoma of the user.

FIGS. 18-24 are schematic perspective illustrations showing embodiments of the system 15 of the disclosure and explaining one exemplary procedure of using the applicator 22 to apply embodiments of a flushable hood-like element 24 of the stoma cover 20 of the system 15 of the disclosure, including steps of preparing and handling the peristomal skin of the user. FIGS. 18-24 also show an exemplary protective sheet (not forming part of the claimed subject matter of the disclosure) held in place over an edge of the waist lining of the user's pants.

Figure 18:
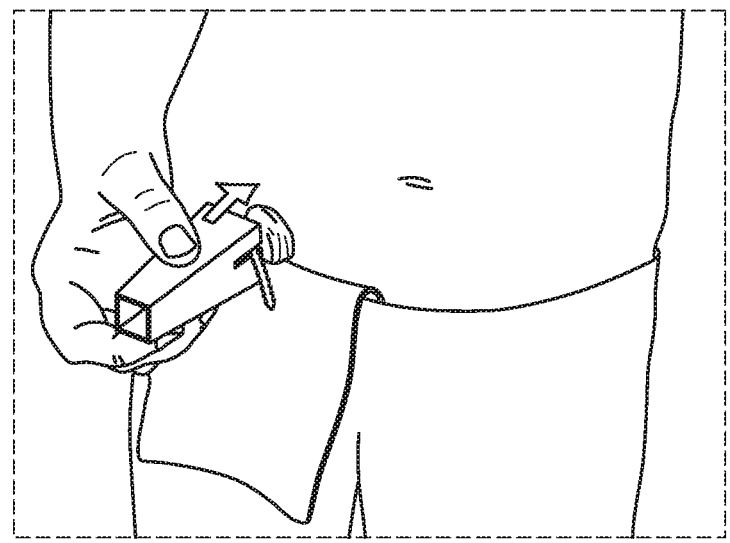
FIGS. 18-24 are schematic perspective illustrations showing embodiments of a system of the disclosure and explaining one exemplary procedure of using the applicator to apply a flushable hood-like element of a stoma cover.

FIG. 18 illustrates a situation where a user has removed the used ostomy appliance from the skin surface, has cleaned the peristomal skin area around the stoma and is ready to use the applicator 22 of the system to apply a stoma cover 20 including a flushable hood-like element 24 over the stoma.

Figure 19:
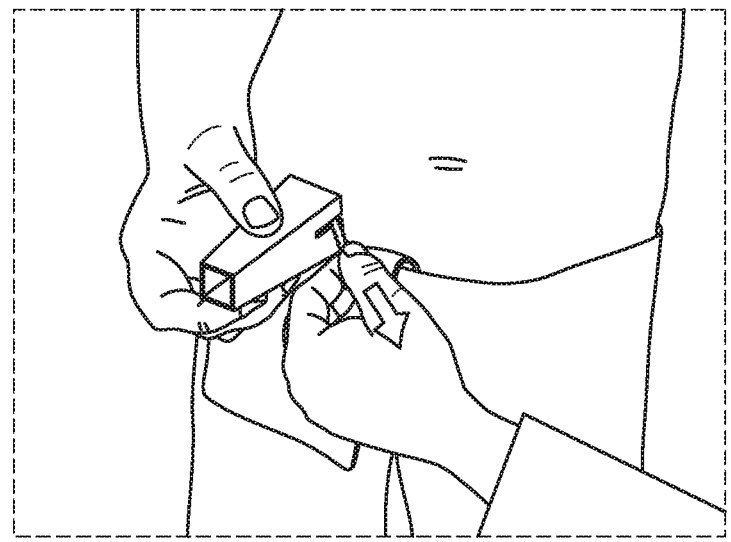

FIG. 19 illustrates a situation where the user is using one hand to hold the applicator 22 with a stoma cover 20 including a flushable hood-like element 24 over the stoma, and using the fingers of the other hand to exert a pull on a pulling strip 80 of the adjustable proximal end portion 26 of the flushable hood-like element 24. The pulling strip extends through a slot 96 in a wall 35 of the oblong element of the applicator 22 and is therefore easily accessible and gripped by the user. By applying finger-pressure to an external surface of the applicator 22, the user further helps to release the releasable stoma cover 20 from the applicator 22.

Figure 20:
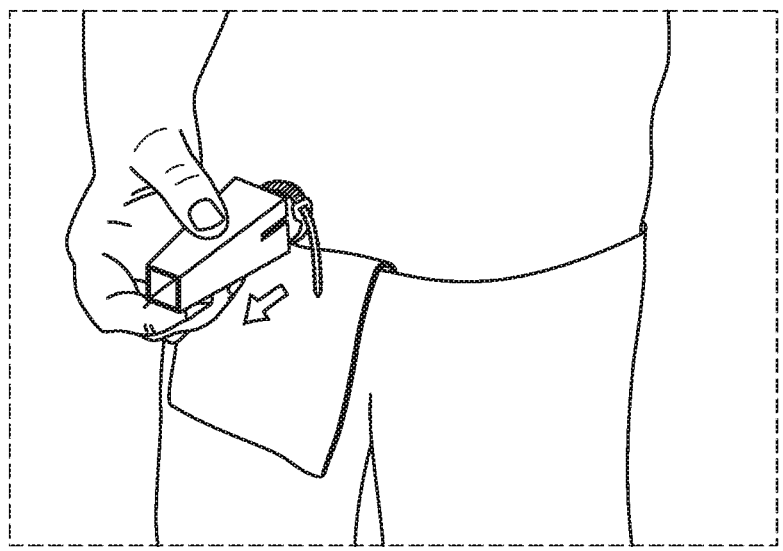

FIG. 20 illustrates a situation where the stoma cover 20 including the flushable hood-like element 24 is being released from the applicator 22 and applied over the stoma. The applicator 22 is being removed by the user and can for example be discarded. The stoma cover 20 including the pulling strip 80 is now located over the stoma.

Figure 21:
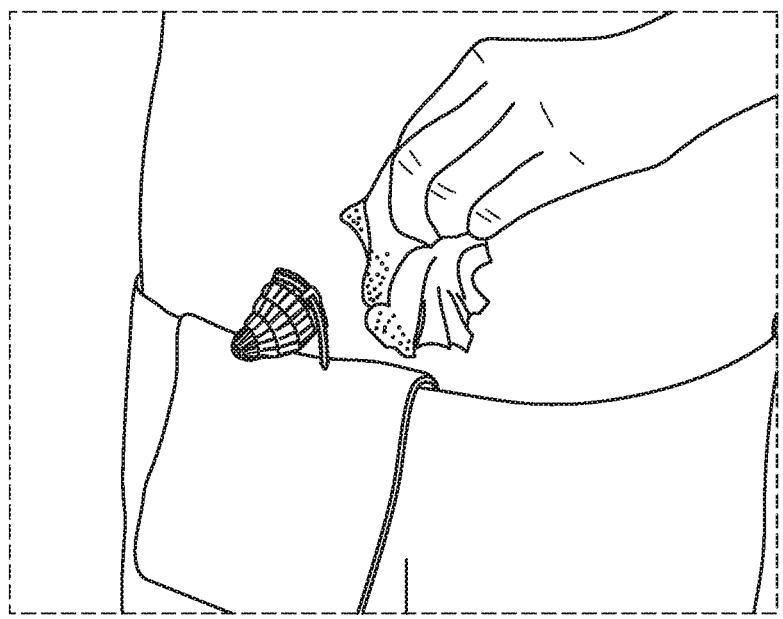

FIG. 21 illustrates how the stoma cover 20 including the flushable hood-like element 24 and the pulling strip 80 is now in place to snugly fit over the stoma, and the user can perform any potentially further required cleaning action in the peristomal skin area.

Figure 22:
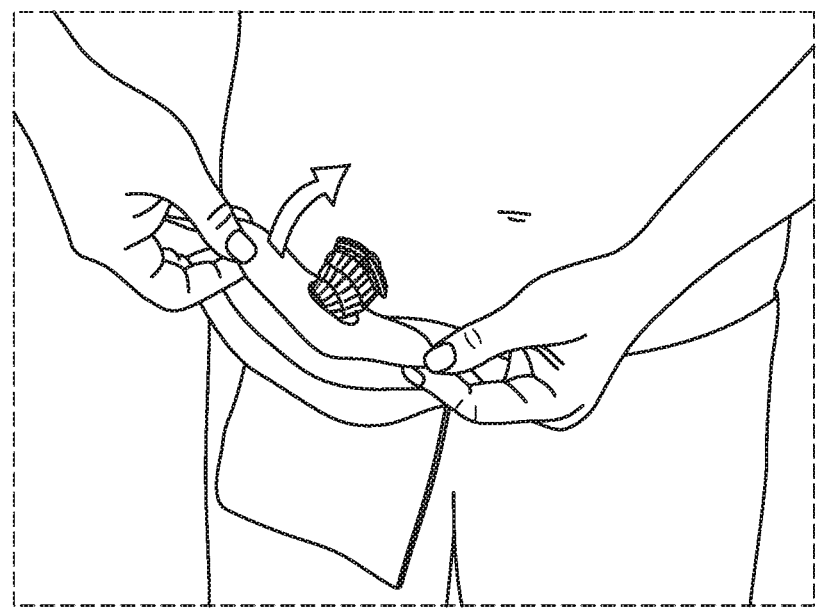

FIG. 22 illustrates how the stoma cover 20, including the flushable hood-like element 24, serving as a temporary covering of the stoma during exchange of the ostomy appliance remains in place over the stoma, when the user applies the fresh ostomy appliance to the peristomal skin surface, and without any contamination or soiling of the peristomal skin area or the adhesive plate of the ostomy appliance from stomal output or mucus. FIG. 22 further schematically illustrates how the flushable hood-like element 24 of the stoma cover 20 can assist the user in guiding the adhesive plate of the fresh ostomy appliance optimally in place around the stoma, because the stoma cover 20 "remaining in place" is believed to provide an increased or improved three-dimensional perception of the stomal area in the user's mind.

Figure 23:
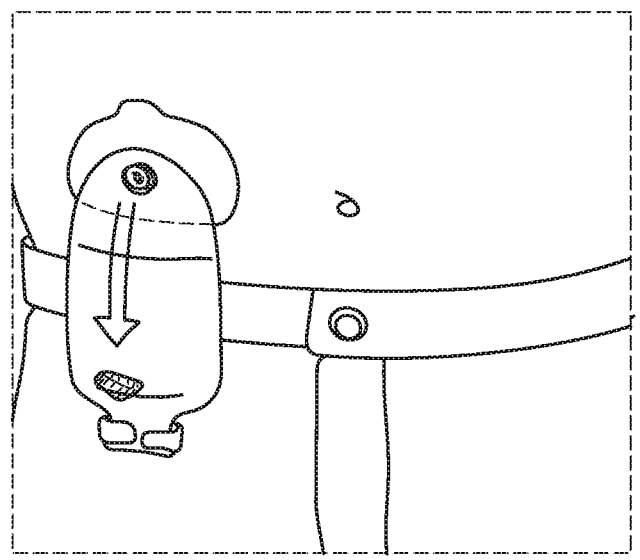

FIG. 23 schematically illustrates how the flushable hood-like element 24 of the stoma cover 20 can be released into the collecting bag of the fresh ostomy appliance. Typically, this occurs with a relatively short time frame after applying the fresh ostomy appliance, such as within about one hour (or sooner) thereof.

Figure 24:
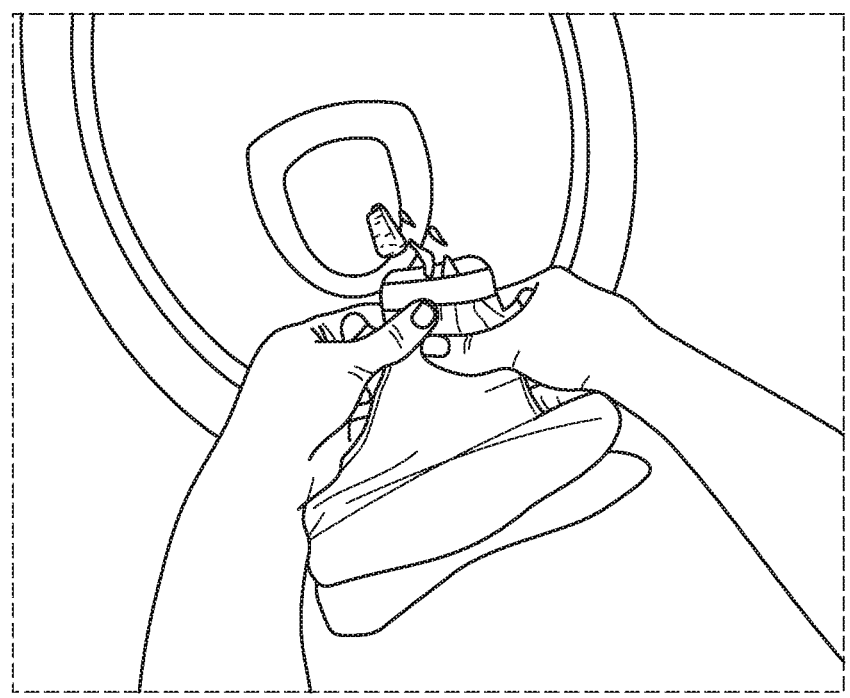

FIG. 24 schematically illustrates how the flushable hood-like element 24 of the stoma cover 20 can be emptied out of an openable discharge portion of a collecting bag of an ostomy appliance and into a toilet, whereby the flushable hood-like element 24 can be discharged into the sewer system. While the advantages of a stoma cover including the flushable hood-like element 24 of the disclosure are in no way limited to use with ostomy appliances including a discharge portion for discharging collected stomal output (without exchanging the ostomy appliance), it is particularly advantageous for users using these types of ostomy appliances. These users are often urostomists or ileostomists who benefit greatly from frequently emptying the often very fluid stomal output out of the collecting bag via a discharge opening. A flushable hood-like element of the stoma cover of the system of the disclosure means that these users do not have to be concerned with removing the temporary stoma cover again, once it has been applied.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. A stoma cover adapted to cover a stoma during an exchange of an ostomy appliance, the stoma cover comprising:
   a hood extending between a proximal end and a closed distal end;
   an adjustment band connected to the proximal end to configure the proximal end of the hood to adjust between a first open size adapted for placement over the stoma and a second size that is smaller than the first open size, where the second size is adapted to secure the hood relative to a root portion of the stoma; and
   a moisture absorbing material disposed inside of the hood;
   wherein the moisture absorbing material is provide to absorb stomal output exuding from a meatus of the stoma.

2. The stoma cover of claim 1, wherein the adjustment band is an elastic band.

3. The stoma cover of claim 1, wherein the adjustment band comprises a pull strip secured to the proximal end of the hood.

4. The stoma cover of claim 1, further comprising:
   a pocket formed along a portion of the proximal end of the hood;
   wherein the adjustment band comprises a pull strip disposed within the pocket, where the pull strip provides a free end adapted to be pulled to adjust the proximal end of the hood to the second size.

5. The stoma cover of claim 1, wherein the moisture absorbing material is cellulose.

6. The stoma cover of claim 1, wherein the moisture absorbing material is polyvinyl alcohol.

7. The stoma cover of claim 1, wherein the moisture absorbing material is a nonwoven material formed of cellulose, polyvinyl alcohol, and combinations of cellulose and polyvinyl alcohol.

8. The stoma cover of claim 1, wherein the hood is formed of a nonwoven fabric and the moisture absorbing material is disposed inside of the nonwoven fabric.

9. The stoma cover of claim 1, wherein the hood is a layered structure comprising:
   a nonwoven fabric exterior; and
   a moisture impermeable material disposed proximal and inside of the nonwoven fabric exterior;
   wherein the moisture absorbing material is disposed proximal and inside of the moisture impermeable material.

10. The stoma cover of claim 9, wherein the moisture impermeable material is formed of polypropylene, polyethylene, thermoplastic elastomer, and combinations of polypropylene, polyethylene, and thermoplastic elastomer.

11. The stoma cover of claim 1, wherein the moisture absorbing material has an absorption capacity in a range from 0-100 ml.

12. The stoma cover of claim 1, wherein the moisture absorbing material has an absorption capacity in a range from 5-15 ml.

13. The stoma cover of claim 1, wherein the hood is formed of a water-soluble polymer that configures the hood to be water flushable in a toilet.

* * * * *